US006335185B1

(12) United States Patent
Rancourt et al.

(10) Patent No.: US 6,335,185 B1
(45) Date of Patent: Jan. 1, 2002

(54) BACTERIOPHAGE VECTORS GENERATED BY BACTERIOPHAGE/PLASMID RECOMBINATION

(75) Inventors: Derrick E. Rancourt, Calgary (CA); Teruhisa Tsuzuki, Fukuoka (JP)

(73) Assignee: University Technologies International Inc., Calgary (CA)

( * ) Notice: Subject to any disclaimer, the term of this patent is extended or adjusted under 35 U.S.C. 154(b) by 0 days.

(21) Appl. No.: 09/240,661

(22) Filed: Feb. 2, 1999

Related U.S. Application Data
(60) Provisional application No. 60/073,528, filed on Feb. 3, 1998.

(51) Int. Cl.[7] .................. C12N 15/64; C12N 15/09; C12N 1/20; C12N 7/01; C07H 21/04

(52) U.S. Cl. ............... 435/91.4; 435/235.1; 435/320.1; 435/471; 435/472; 435/475; 435/243; 435/252.33; 435/252.3; 536/23.1

(58) Field of Search .................. 435/91.4, 320.1, 435/471, 472, 475, 243, 252.33, 252.3, 235.1; 536/23.1

(56) References Cited

U.S. PATENT DOCUMENTS

| 4,713,337 A | 12/1987 | Jasin et al. |
| 5,310,671 A | 5/1994 | Binns et al. |
| 5,464,764 A | 11/1995 | Capecchi et al. |
| 5,487,992 A | 1/1996 | Capecchi et al. |
| 5,580,717 A | 12/1996 | Dower et al. |
| 5,580,734 A | 12/1996 | Treco et al. |
| 5,631,153 A | 5/1997 | Capecchi et al. |
| 5,789,215 A | 8/1998 | Berns et al. |
| 6,090,554 A | 7/2000 | Woychik |
| 6,090,629 A | 7/2000 | Woychik |

FOREIGN PATENT DOCUMENTS

| EP | 0 814 165 A | 12/1997 |
| JP | 61 162186 | 7/1986 |
| WO | WO 91/18093 A | 11/1991 |
| WO | WO 95/03400 | 2/1995 |
| WO | WO 95/14769 | 6/1995 |
| WO | WO 96/14436 | 5/1996 |
| WO | WO 97/49820 A | 12/1997 |

OTHER PUBLICATIONS

Matsuzaki, H. et al., "Chromosome Engineering in *Saccharomyces cerevisiae* by Using a Site–Specific Recombination System of a Yeast Plasmid" *J. Bacteriol.*, 172: 610–618 (1990).

Sternberg, N., "Bacteriophage P1 Cloning System for the Isolation, Amplification and Recovery of cDBA Fragments As Large As 100 Kilobase Pairs" *Proc. Natl. Acad. Sci. USA*, 87: 103–107 (1990).

Capecchi, M.R. "The New Mouse Genetics: Altering the Genome by Gene Targeting" *Trends Genet.*, 5(3):70–76(1989).

Capecchi, M.R., "Altering the Genome by Homologous Recombination"*Science*, 244: 1288–1292(1989).

Capecchi, M.R., "Targeted Gene Replacement" *Scientific American*, 34–41 (Mar. 1994).

(List continued on next page.)

Primary Examiner—David Guzo
Assistant Examiner—Gerald G. Leffers, Jr.
(74) Attorney, Agent, or Firm—Burns, Doane Swecker & Mathis, LLP

(57) ABSTRACT

The present invention relates to methods for the generation of lambda (λ) or P1 bacteriophage vectors useful in targeted mutagenesis of eukaryotic cells and the expression of genes and proteins, methods for the identification of a λ or P1 bacteriophage vector having a desired nucleic acid from an assortment or library of bacteriophage each having a different nucleic acid insert and the use of such vectors in gene targeting and the expression of genes and protein.

15 Claims, 9 Drawing Sheets

OTHER PUBLICATIONS

Chisaka et al., "Regionally restricted developmental defects resulting from the targeted disruption of the mouse homeobox gene hox 1.5" *Nature,* 350:473–479 (1991).

Deng, et al., "Reexamination of Gene Targeting Frequency as a Function of the Extent of Homology Between the Targeting Vector and the Target Locus" *Mol. Cell. Biol.,* 12(8):3365–3371 (1992).

Deng, et al., "Location of Crossovers during Gene Targeting with Insertion and Replacement Vectors" *Mol. Cell. Biol.* 13(4): 2134–2140 (1993).

Elledge et al., "Phasmid Vectors for Identification of Genes by Complementation of *Escherichia coli* Mutants" *J. of Bact.*162(2)777–783 (1985).

Garkavtsev et al., "Suppression of the novel growth inhibitor p33$^{ING1}$ promotes neoplastic transformation" *Nature Genetics* 14:415–420 (1996).

Gorry et al., "The cellular retinoic acid binding protein I is dispensable" *Proc. Natl. Acad. Sci.,* 91:9032–9036 (1994).

Haggard–Ljungquist et al., "The P2 phage old gene: sequence, transcription and translational control" *Gene,* 85:25–33 (1989).

Hanks et al., "Rescue of the En–1 Mutant Phenotype by Replacement of En–1 with En–2" *Science,* 269:679–682 (1995).

Hasty et al., "Introduction of a subtle mutation into the Hox–2.6 locus in embryonic stem cells" *Nature,* 350:243–246 (1991).

Hasty et al., "Gene targeting vectors for mammalian cells" In *Gene Targeting: A Practical Approach,* Alexandra L. Joyner, Ed., Univ. Press, New York pp. 1–31.

Hong et al., "Protection from proteolysis using a T4::T7–RNAP phage expression–packaging–processing system" *Gene* 162:5–11 (1995).

Humphries et al, "Retinopathy induced in mice by targeted disruption of the rhodopsin gene" *Nature Genet.,* 15:216–219 (1997).

Kreuzer et al., "Integration of Plasmids Into the Bacteriophage T4 Genome" *Genetics* 138: 983–992 (1994).

Leenhouts et al., "Replacement Recombination in *Lactococcus lactis*" *Journal of Bact.* 173(15):4794–4798 (1991).

Lin et al., "Genomic cloning and preliminary characterization of the human thymidine kinase gene" *Proc. Natl. Acad. Sci.* 80:6528–6532 (1983).

Lutz, et al., "Syrinx 2A: An improved λ phage vector designed for screening DNA libraries by recombination in vivo" *Proc. Natl. Acad. Sci.,* 84:4379–4383 (1987).

Mackow et al., "Identification and Baculovirus Expression of the VP4 Protein of the Human Group B Rotavirus ADRV" *Journal of Virol.* 67(5):2730–2738 (1993).

Mansour, et al., "Disruption of the proto–oncogene int–2 in mouse embryo–derived stem cells: a general strategy for targeting mutations to non–selectable genes" *Nature,* 336:348–352 (1988).

Mansour et al., "Introduction of a lacZ reporter gene into the mouse int–2 locus by homologous recombination" *Proc. Natl. Acad. Sci.* 87:7688–7692 (1990).

Mombaerts et al., "Creation of a large genomic deletion at the T–Cell antigen receptor β–subunit locus in mouse embryonic stem cells by gene targeting" *Proc. Natl. Acad. Sci.,* 88:3084–3087 (1991).

Maruyama et al., "A selective λ phage cloning vector with automatic excision of the insert in plasmid" *Gene* 120: 135–141 (1992).

McCarthy et al., "Sensitive homologous recombination strand–transfer assay: Partial purification of a *Drosophila melanogaster* enzyme and detection of sequence efforts on the strand–transfer activity of a RecA protein" *Proc. Natl. Acad. Sci. USA,* 85:5854–5858 (1988).

Nagy et al., "Perspective Series: Molecular Medicine in Genetically Engineered Animals" *J. Clin Invest.,* 98(11):S31–S35 (1996).

Nehls et al., "Two Large Insert Vectors, λPS and λKO, Facilitate Rapid Mapping and Targeted Disruption of Mammalian Genes" *BioTechniques,* 17(4):770–775 (1994).

Nohmi et al., "A New Transgenic Mouse Mutagenesis Test System Using Spi⁻ and 6–Thioguanine Selections" *Environ. and Mol. Mutagenesis* 28:465–470 (1996).

Ramirez–Solis et al., "Chromosome engineering in mice" *Nature,* 378:720–724 (1995).

Rancourt, et al., "Genetic interaction between hoxb–5 and hoxb–6 is revealed by nonallelic noncomplementation" *Genes & Dev.,* 9:108–122 (1995).

Sambrook et al., *Molecular Cloning: A Laboratory Manual.* Cold Springs Harbor University Press, Cold Spring Harbor, NY (1989).

Sander et al., "rpsL⁺: a dominant selectable marker for gene replacement in mycobacteria" *Mol. Mirobiology* 16(5):991–1000 (1995).

Seed, B., "Purification of genomic sequences from bacteriophage libraries by recombination and selection in vivo" *Nucleic Acids Res.,* 11(8):2427–2445 (1983).

Shen et al., "Homologous Recombination in *Escherichia Coli* Dependence on Substrate Length and Homology" *Genetics,* 112:441–457 (1986).

Singer et al., "Phage T4 expression vector: protection from proteolysis" *Gene,* 106:1–6 (1991).

Sternberg et al., "Display of peptides and proteins on the surface of bacteriophage λ." *PNAS USA* 92:1609–1613 (1995).

Thomas et al., "Site–Directed Mutagenesis by Gene Targeting in Mouse Embryo–Derived Stem Cells" *Cell,* 51:503–512 (1987).

Thomas et al., "High Fidelity Gene Targeting in Embryonic Stem Cells by Using Sequence Replacement Vectors" *Mol. and Cell. Bio.,* 12(7):2919–2923 (1992).

Tsien et al., "Subregion– and Cell Type–Restricted Gene Knockout in Mouse Brain" *Cell,* 87:1317–1326 (1996).

Tsuzuki et al., "Targeted disruption of the DNA repair methyltransferase gene renders mice hypersenitive to alkylating agent" *Carcinogenesis* 17(6):1215–1220 (1996).

Tsuzuki et al., "Targeted disruption of the Rad51 gene leads to lethality in embryonic mice" *Proc. Natl. Acad. Sci USA.*93:6236–6240 (1996).

Tsuzuki et al., "Embryonic stem cell gene targeting using bacteriophage λ vectors generated by phage–plasmid recombination" *Nucl. Acids Res.* 26(4):988–993 (1998).

Umene et al., "Lambda Bacteriophage–Mediated Transduction of ColE1 Deoxyribonucleic Acid Having a Lambda Bacteriophage–Cohesive End Site: Selection of Packageable–Length Deoxyribonucleic Acid"*J. Bacteriol.,* 139(3):738–747 (1979).

Valancius et al., "Testing an 'In–Out' Targeting Procedure for Making Subtle Genomic Modifications in Mouse Embryonic Stem Cells" *Mol and Cell.Bio.* 11(3):1401–1408 (1991).

Weber et al., "Mutations in the tissue inhibitor of metalloproteinases–3(TIMP3) in patients with Sorsby's fundus dystrophy" *Nature Genetics* 8:352–356 (1994).

Wei et al., "Molecular Cloning and Transcriptional Mapping of the Mouse Cellular Retinoic Acid–Binding Protein Gene" *DNA Cell. Biol.*, 9(7):471–478.(1990).

Winston et al., "Eviction and Transplacement of Mutant Genes in Yeast" *Methods in Enzymology* 101:211–227 (1983).

Yeom et al., "Structure, expression and chromosomal location of the Oct–4 gene" *Mech. Dev.* 35:171–179 (1991).

Zabarovsky et al., "An improved technique for the efficient construction of gene libraries by partial filling–in of cohesive ends" *Gene* 42:119–123 (1986).

Zheng, H. and Wilson, J.H. "Gene targeting in normal and amplified cell lines" *Nature,* 344:170–173 (1990).-

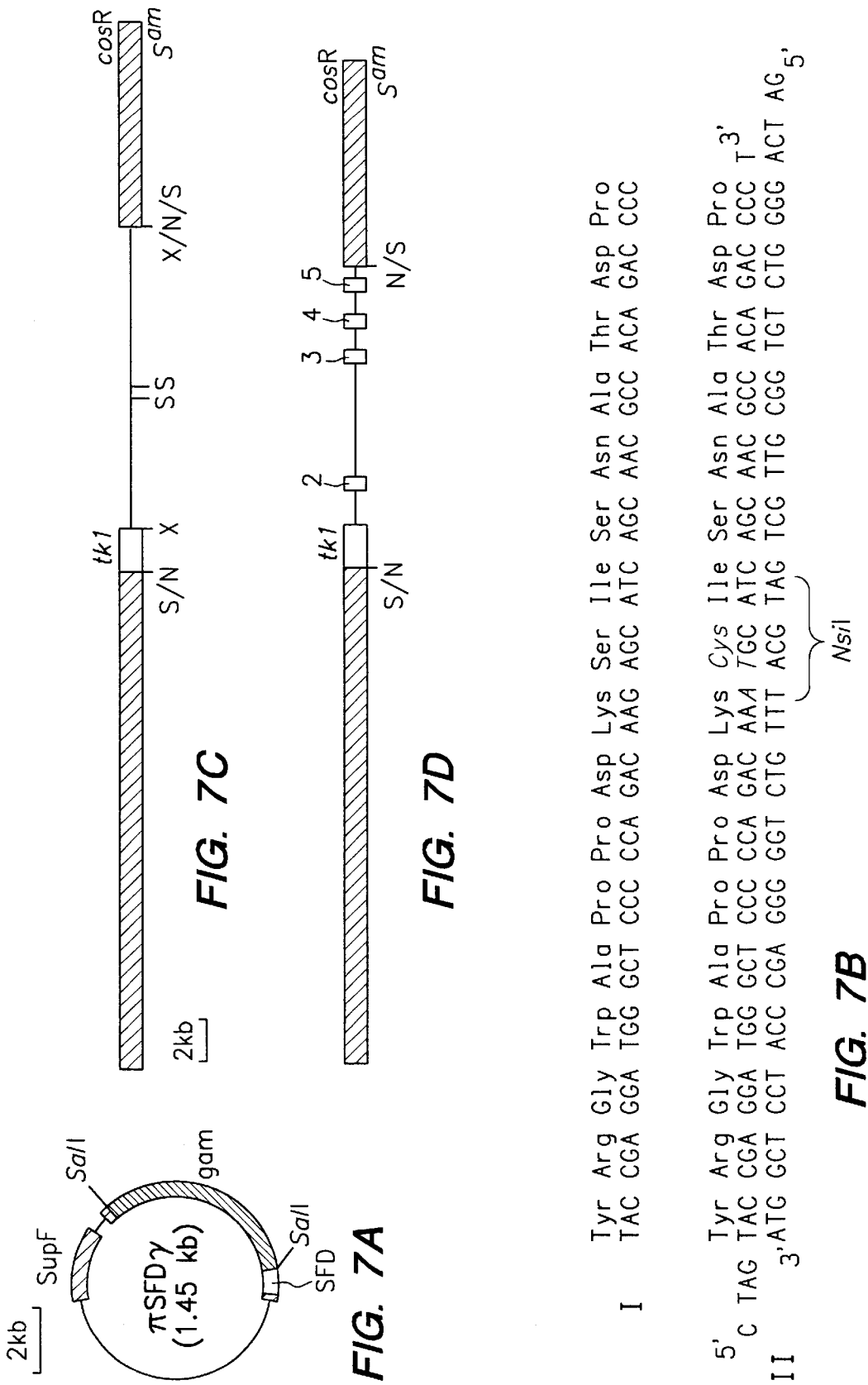

FIG. 8C
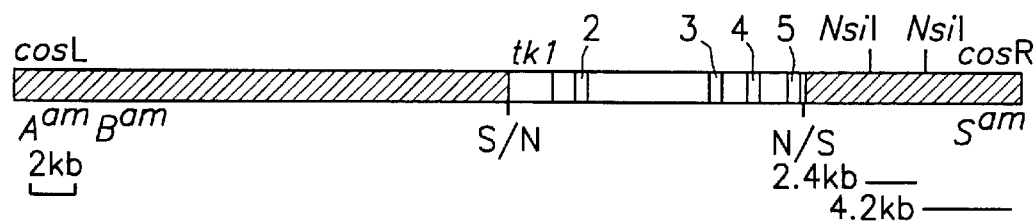
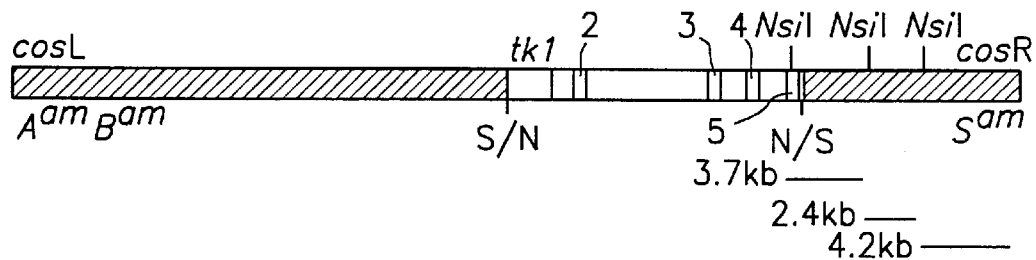

SEQUENCE LISTING

<160> NUMBER OF SEQ ID NOS: 7

<210> SEQ ID NO 1
<211> LENGTH: 51
<212> TYPE: DNA
<213> ORGANISM: Artificial Sequence
<220> FEATURE:
<221> NAME/KEY: CDS
<222> LOCATION: (1)..(51)
<223> OTHER INFORMATION: Description of Artificial Sequence: Bacteriophage vectors

<400> SEQUENCE: 1

```
tac cga gga tgg gct ccc cca gac aag agc atc agc aac gcc aca gac      48
Tyr Arg Gly Trp Ala Pro Pro Asp Lys Ser Ile Ser Asn Ala Thr Asp
 1               5                  10                  15 ccc                                                                   51
Pro

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence:
      Bacteriophage vectors

<400> SEQUENCE: 2

Tyr Arg Gly Trp Ala Pro Pro Asp Lys Ser Ile Ser Asn Ala Thr Asp
 1               5                  10                  15

Pro

<210> SEQ ID NO 3
<211> LENGTH: 56
<212> TYPE: DNA
<213> ORGANISM: Artificial Sequence
<220> FEATURE:
<221> NAME/KEY: CDS
<222> LOCATION: (5)..(55)
<223> OTHER INFORMATION: Description of Artificial Sequence:
      Bacteriophage vectors

<400> SEQUENCE: 3 ctag tac cga gga tgg gct ccc cca gac aaa tgc atc agc aac gcc aca      49
     Tyr Arg Gly Trp Ala Pro Pro Asp Lys Cys Ile Ser Asn Ala Thr
      1               5                  10                  15 gac ccc t                                                             56
Asp Pro <210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence:
      Bacteriophage vectors

<400> SEQUENCE: 4

Tyr Arg Gly Trp Ala Pro Pro Asp Lys Cys Ile Ser Asn Ala Thr Asp
 1               5                  10                  15

Pro

<210> SEQ ID NO 5
<211> LENGTH: 56
<212> TYPE: DNA
<213> ORGANISM: Artificial Sequence
<220> FEATURE:
<223> OTHER INFORMATION: Description of Artificial Sequence:
      Bacteriophage vectors

<400> SEQUENCE: 5
atggctccta cccgagggggg tctgtttacg tagtcgttgc ggtgtctggg gactag        56

<210> SEQ ID NO 6
<211> LENGTH: 57
<212> TYPE: DNA
<213> ORGANISM: Artificial Sequence
<220> FEATURE:
```

-continued

```
<223> OTHER INFORMATION: Description of Artificial Sequence:
      Bacteriophage vectors

<400> SEQUENCE: 6
aattcgcgct ccctgccgac tttcccatcg accccaacga gcccacgtac tgtctga         57

<210> SEQ ID NO 7
<211> LENGTH: 56
<212> TYPE: DNA
<213> ORGANISM: Artificial Sequence
<220> FEATURE:
<223> OTHER INFORMATION: Description of Artificial Sequence:
      Bacteriophage vectors

<400> SEQUENCE: 7
cgcgagggac ggctgaaagg gtagctgggg ttgctcgggt gcatgacaga ctctag          56
```

BACTERIOPHAGE VECTORS GENERATED BY BACTERIOPHAGE/PLASMID RECOMBINATION

CROSS-REFERENCE TO RELATED APPLICATIONS

This application claims the benefit of U.S. Provisional Application No. 60/073,528 filed on Feb. 3, 1998, which is incorporated by reference herein in its entirety.

BACKGROUND OF THE INVENTION

1. Field of the Invention

The present invention relates to methods for the generation of lambda (λ) or P1 bacteriophage vectors useful in targeted mutagenesis of eukaryotic cells and the expression of genes and proteins, methods for the identification of a λ or P1 bacteriophage vector having a desired nucleic acid from an assortment or library of bacteriophage each having a different nucleic acid insert and the use of such vectors in gene targeting and the expression of genes and protein.

2. Description of the Related Art

The present invention provides a method for the construction of a λ or P1 bacteriophage vector using bacteriophage/plasmid recombination and selection for double-crossover bacteriophage recombinants.

Vectors have traditionally been generated through restriction enzyme digestion of the vector and religation with the desired target nucleic acid. In general, two types of problems are encountered in the construction of vectors by this method. First, plasmid vectors may be undesirable because specific eukaryotic genomic regions can undergo rearrangements in plasmid vectors. Therefore genomic regions may be difficult to clone either on their own or in combination with eukaryotic selectable marker genes, such as neo or tk. Secondly, larger sizes of target DNA sequences are desirable. However, the larger the DNA sequence, the more restriction enzyme sites present in the DNA. For cloning purposes, suitable restrictions sites are low frequency sites located on either side of the target nucleic acid sequence. Therefore, because of the large number of restriction enzyme sites in large genomic fragments, the use of such fragments in vectors means that there is often very few or no suitable restriction sites for inserting foreign DNA fragments, such as positive selectable marker genes or small mutations.

Accordingly, it would be desirable to develop a method for the generation of vectors capable of accepting large genomic fragments without rearrangement and without the need for suitable restriction enzyme sites.

Bacteriophage/plasmid recombination has been used to screen and isolate targeted λ phage from genomic libraries (15, 17). For example, a λ genomic library (bearing amber mutations) was passaged over a rec$^+$ bacterial strain bearing a small supF (amber suppressing) recombination plasmid having sequence homologous to the desired gene. Homology in the recombination plasmid, usually derived from a cDNA sequence, directed the plasmid to integrate into the phage by a single crossover, thereby generating supF bearing phage recombinants capable of growing on a suppressor free (sup$^0$) host. Depending on homology length, the recombination plasmid can integrate at a frequency of ~10$^{-2}$. One of the difficulties with this method of bacteriophage/plasmid recombination is that it generated single cross-over recombinants. Single cross-over recombinants are generally considered undesirable because of the presence of plasmid sequences and the partial duplication of the target nucleic acid.

Accordingly, it would be beneficial to develop a method for the identification of a recombinant bacteriophage from a library through plasmid/phage recombination which method resulted in the isolation of the original bacteriophage without the insertion of the plasmid nucleic acid sequences.

Eukaryotic gene targeting involves the selection for homologous recombination events between DNA sequences residing in the genome of a eukaryotic cell or organism and newly introduced DNA sequences. This provides a means for systematically altering the genome of a eukaryotic cell or organism. For mammalian systems, laboratories have reported the insertion of exogenous DNA sequences into specific sites within the mammalian genome by way of homologous recombination. For example, targeted mutagenesis allows specific mutations to be engineered into the mouse germline via homologous recombination of exogenously-altered DNA in embryonic stem (ES) cells (1, 2). Using this technology, the function of any cloned gene may be examined by its disruption in mice. Thus, gene targeting is a critical experiment in molecular medicine, and is used, for example, to mimic human mutations in the mouse for the generation of experimental therapeutic models (3).

The original and still the most prevalent gene targeting approach, "the knockout", uses a replacement plasmid vector to direct a positive selectable marker (i.e. neomycin resistance gene) into a specific chromosomal location via either double-reciprocal exchange or gene conversion (4). Positive-negative selection vectors have been used for gene targeting (26). Many sophisticated variations on this original technique have become available, including the generation of point mutations, deletions and translocations and gene substitutions (5–9). Further, the application of cre recombinase from bacteriophage P1 allows additional genomic alterations at loxP target sequences following gene targeting so that mutations can be made tissue- or development-specific (10).

Although targeted mutagenesis provides a powerful tool for the analysis of gene function, it is a complex and time-consuming procedure. While methods of improving the efficiency of generating targeted ES cell lines (11) and mutant mice (12) have become available, little has been done to streamline the construction of the targeting vector. Currently the rate determining step in any gene targeting experiment is the construction of the targeting vector.

Accordingly, there is a need to develop a method to generate targeting vectors which does not require as much cumbersome restriction enzyme methodology and yet would yield targeting vectors which are efficient in inserting larger fragments of the modified nucleic acid into the desired site in the eukaryotic cell.

Further advantages of the present invention will become apparent from the following description of the invention with reference to the attached drawings.

SUMMARY OF THE INVENTION

This invention describes how double-crossover bacteriophage generated by bacteriophage/plasmid recombination can be selected through the use of double-crossover selectable markers present on the plasmid vector. The present invention is directed to the generation of λ or P1 bacteriophage vectors using this method. The present invention is also directed to a method for screening a λ or P1 bacteriophage library for the identification of a recombinant bacteriophage having the desired target sequence and to the generation of bacteriophage targeting vectors.

One aspect of this invention is directed to a method for generating recombinant λ or P1 bacteriophage vectors, which method comprises
(a) providing a λ or P1 bacteriophage nucleic acid sequence comprising a first target nucleic acid sequence;
(b) providing a plasmid comprising a nucleic acid sequence encoding a second modified target nucleic acid sequence, and a double-crossover selectable marker gene wherein the second modified target nucleic acid sequence is substantially homologous over a portion of its length to the first target nucleic acid sequence;
(c) contacting the bacteriophage and the plasmid under conditions such that homologous recombination between the first target nucleic acid sequence and the second target nucleic acid sequence occurs;
(d) selecting for double-crossover recombinant bacteriophage by placing the bacteriophage from step (c) under conditions such that bacteriophage having the double-crossover selectable marker are unable to replicate and isolating the double-crossover recombinant bacteriophage. The double-crossover selectable marker gene may be gam where the λ recombinant bacteriophage is grown in a P2 lysogenic bacterial cell. The double-crossover selectable marker may be any large nucleic acid sequence where the λ or P1 recombinant bacteriophage is placed under a size restriction, such as a requirement to be packaged in a viral coat or particle.

In this method, the plasmid may further comprise a prokaryotic positive selectable marker inserted into the target nucleic acid sequence. The prokaryotic positive selectable marker is preferably supF or supE genes where the bacteriophage has amber mutations in essential genes. The plasmid may further comprise a eukaryotic positive selectable marker inserted into the target nucleic acid sequence. Preferably, the eukaryotic positive selectable marker gene may be the Neo, Hyg, hisD, Gpt, Ble,or Hprt genes. The bacteriophage may further comprise a eukaryotic negative selectable marker. Preferably, the eukaryotic negative selectable marker is the tk1 or tk2 genes.

Another aspect of this invention is a recombinant λ or P1 bacteriophage nucleic acid comprising a nucleic acid sequence encoding a positive eukaryotic selectable marker located within a target nucleic acid sequence and a positive prokaryotic selectable marker. Preferably the bacteriophage further comprises a nucleic acid sequence encoding a negative eukaryotic selectable marker positioned 5' or 3' to the target nucleic acid sequence. Also contemplated are bacteriophage particles comprising the recombinant bacteriophage nucleic acid. Also contemplated is a bacteriophage wherein the target nucleic acid sequence is further modified by insertions, deletions or substitutions.

In another aspect of this invention the recombinant bacteriophage nucleic acid is isolated from the bacteriophage particle and restriction enzyme digested to remove the bacteriophage arm nucleic acid.

Another aspect of this invention is a method for insertion of a modified target nucleic acid sequence into a eukaryotic cell genome through homologous recombination comprising providing a recombinant bacteriophage nucleic acid comprising a nucleic acid sequence encoding a positive eukaryotic selectable marker gene located within a modified target nucleic acid sequence; and contacting a eukaryotic cell with the bacteriophage nucleic acid under conditions whereby the modified target nucleic acid sequence in the bacteriophage undergoes homologous recombination with the target nucleic acid sequence in the eukaryotic cell. Preferably the bacteriophage further comprises a nucleic acid sequence encoding a negative eukaryotic selectable marker gene positioned 5' or 3' to the target nucleic acid. Preferably, the recombinant bacteriophage nucleic acid is packaged in a virion particle prior to contacting the eukaryotic cell.

Another aspect of this invention is a method for selection of a bacteriophage having a desired target nucleic acid sequence from an assortment of bacteriophage wherein each of the bacteriophage comprise a different nucleic acid insert comprising the following steps:

providing a plasmid, which plasmid comprises a portion of the desired target nucleic acid sequence, a positive selectable marker gene and a double-crossover selectable marker, providing an assortment of bacteriophage comprising different nucleic acid inserts;

contacting the assortment of bacteriophage with the plasmid under conditions such that homologous recombination between the target nucleic acid sequence on the plasmid and the desired target nucleic acid sequence on the bacteriophage can occur;

growing the bacteriophage in bacterial cells under conditions wherein those bacteriophage which have recombined with the plasmid are able to replicate; growing the bacteriophage in bacterial cells under conditions wherein those bacteriophage lacking the double crossover selectable marker are able to replicate; and identifying those bacteriophage as comprising the desired target nucleic acid.

BRIEF DESCRIPTION OF THE DRAWINGS

FIG. 7A illustrates the restriction map of πSFDγ.

FIG. 7B is the sequence of an oligonucleotide with homology to the fifth exon of TIMP3 and the corresponding amino acids (I) [SEQ ID NOS: 1 & 2] and the sequence of the oligonucleotide and protein with the 2 bp substitution (II) [SEQ ID NOS: 3 to 5].

FIG. 7C illustrates the restriction map of λTK.

FIG. 7D illustrates the restriction map of λTK:TIMP3.

FIG. 8C is a NsiI restriction map of the two revertent types.

DETAILED DESCRIPTION OF THE INVENTION

Figure 1A:
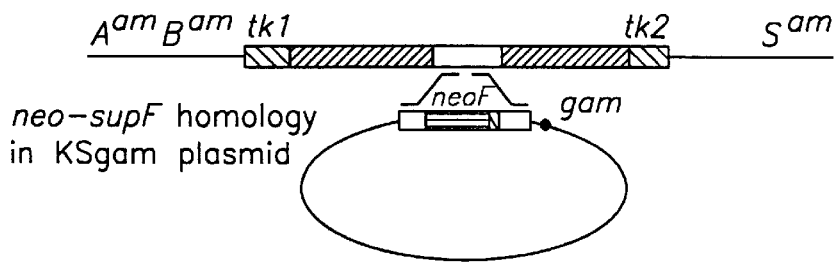
FIG. 1A shows a double-crossover recombination event with a neo-supF ("neoF") split homology bearing plasmid.

The present invention relates to the generation of bacteriophage vectors.

However, prior to discussing this invention in further detail, the following terms will first be defined.

Definitions

The term "target nucleic acid sequence" is a predetermined nucleic acid sequence which is targeted or desired. Target nucleic acid sequences include, but are not limited to, eukaryotic structural genes (i.e. DNA sequences encoding polypeptides including in the case of eukaryotes, introns and exons), regulatory sequences such as enhancers, promoters and the like and other regions within the genome of interest. A target nucleic acid sequence may also be a sequence which has no effect on the function of the host eukaryotic genome. The target nucleic acid sequence on the bacteriophage may be referred to as the "first target nucleic acid sequence". The target nucleic acid sequence on the plasmid may be referred to as the "second target nucleic acid sequence". The target nucleic acid sequence in the eukaryotic genome may be referred to as the "third target nucleic acid sequence".

It is understood that the size of the "first target nucleic acid sequence" in the bacteriophage vector is at least about 500 bp, more preferably at least about 3 kb and most preferably at least about 10 kb. The maximum size of the target nucleic acid sequence will be determined by the size of nucleic acid accepted by the cloning site in the bacteriophage.

On the other hand, the size of the "second target nucleic acid sequence" in the plasmid can be much smaller. It is contemplated that the target nucleic acid sequence on the plasmid can be at least about 25 bp, more preferably 500 bp and most preferably 1 kb.

The term "modified target nucleic acid sequence" refers to a nucleic acid sequence which has been modified by the insertion, deletion and/or substitution of nucleotides. Such insertions may comprise the insertion of a positive eukaryotic or prokaryotic selectable marker gene into the target nucleic acid. Alternatively another endogenous gene sequence may be incorporated into the target nucleic acid in the bacteriophage vector to target its insertion into a different regulatory region of the eukaryotic genome. Further modified target nucleic acid sequences may include exogenous sequences derived from a different species than the target nucleic acid.

When the object of the modification is to disrupt the expression of a particular gene, the positive selectable marker gene is generally contained within an exon of the target nucleic acid sequence which effectively disrupts transcription and/or translation of the targeted nucleic acid sequence. When, however, the object of the modification is to insert an exogenous gene or correct an endogenous gene defect, the modified target nucleic acid sequence will contain the prokaryotic or eukaryotic, positive selectable marker gene in an intron. If the object of the modification is to insert an exogenous gene or a mutation into the target nucleic acid sequence, the modified target nucleic acid sequence will contain the exogenous gene or the mutation. If the object of the modification is to insert a corrected gene into the eukaryotic cell genome, the modified target nucleic acid will contain the native or correct sequence.

The term "targeting vector" refers to a bacteriophage vector which comprises a target nucleic acid sequence. The targeting vector may comprise a modified target nucleic acid sequence comprising a nucleic acid sequence which encodes a positive eukaryotic selectable marker. Preferably the targeting vector further comprises a nucleic acid sequence encoding a negative eukaryotic selectable marker gene which sequence is positioned 5' or 3' to the target nucleic acid sequence.

Recombinant bacteriophage are those bacteriophage comprising a modified target nucleic acid.

The positive and negative selectable markers are chosen such that they are functional in the cells containing the target nucleic acid. Positive and/or negative selectable markers are "functional" in transformed cells if the phenotype expressed by the nucleic acid sequences encoding such selectable markers is capable of conferring either a positive or negative selection characteristic for the cell expressing that nucleic acid sequence.

Thus "positive selection" comprises contacting cells transfected with a targeting vector with an appropriate agent which kills or otherwise selects against cells or bacteriophage not containing a positive selectable marker. "Negative selection" comprises contacting cells transfected with the targeting vector with an appropriate agent which kills or otherwise selects against cells or bacteriophage containing the negative selectable marker. Positive and negative selectable marker genes can be specific for eukaryotic cells, hence "eukaryotic selectable marker gene" or prokaryotic cells, hence "prokaryotic selectable marker gene".

Examples of preferred positive and negative eukaryotic selectable markers are listed in Table I.

TABLE I

| GENE | SELECTIVE AGENT | TYPE OF SELECTION |
| --- | --- | --- |
| Neo | G418 | + |
| Neo | kanamycin | + |
| Hyg | Hygromycin | + |

TABLE I-continued

| GENE | SELECTIVE AGENT | TYPE OF SELECTION |
|---|---|---|
| hisD | Histidinol | + |
| Gpt | Xanthine | + |
| Ble | Bleomycin | + |
| Hprt | Hypoxanthine | + |
| green fluorescent protein | cell sorting | + |
| cell surface proteins | cell sorting | + |
| green fluorescent protein | cell sorting | − |
| cell surface proteins | cell sorting | − |
| HSV-tk | Acyclovir Gancyclovir FIAU | − |
| Hprt | 6-thioguanine | − |
| Gpt | 6-thioxanthine | − |
| Diptheria toxin | None | − |
| Ricin toxin | None | − |
| cytosine deaminase | 5-fluoro-cytosine | − |

Examples of preferred positive prokaryotic selectable marker genes are supF or supE (which allow bacteriophage having amber mutations to grow on a $sup^0$ host bacterial cell).

The term "double-crossover selectable marker" or "recombination selectable marker" refers to a gene or nucleic acid sequence the presence of which on the bacteriophage selects against replication or growth of the bacteriophage under certain conditions. Preferably the double-crossover selectable marker is effective during the lytic cycle of the bacteriophage and does not require lysogeny of the bacteriophage into the bacterial chromosome. The "double-crossover selectable marker" is preferably placed on the plasmid either 5' or 3' to the target nucleic acid sequence. After homologous recombination of the plasmid with the bacteriophage, the bacteriophage is placed under conditions such that bacteriophage having the double-crossover selectable marker are unable to replicate or grow. This selection against bacteriophage having the double-crossover selectable marker will enrich for a double-crossover recombinant bacteriophage. A preferred double-crossover selectable marker is the gam gene where the bacteriophage are passaged through a the P2 lysogenic $sup^0$ E. coli cell (18). Another preferred double-crossover recombination selectable marker is a large nucleic acid sequence present on the plasmid. Bacteriophage incorporating the entire plasmid genome, including this large nucleic acid sequence can not be packaged into a viral particle and accordingly are unable to replicate. Preferably the plasmid is sized such that the total length of the λ bacteriophage nucleic acid and the plasmid nucleic acid will be at least about 50 kb, more preferably at least about 55 kb and most preferably at least about 60 kb. In the case of P1 bacteriophage, the plasmid is preferably sized such that the total length of the P1 bacteriophage nucleic acid and the plasmid nucleic acid will be at least about 110 kb, more preferably at least about 115 kb and most preferably at least about 120 kb. Other preferred double-crossover selectable markers are the old gene for the P2 bacteriophage (19) and the λred gene (18).

"Double-crossover recombinant bacteriophage" are bacteriophage which have undergone homologous recombination with a plasmid having a substantially homologous target nucleic acid sequence in such a manner that there are two recombination events between the target nucleic acid sequences of the plasmid and the phage, such that a portion of the plasmid target nucleic acid sequence replaces that portion of the bacteriophage target nucleic acid sequence. It is contemplated that these two recombination events may occur spaced in time. For example the double-crossover recombination can occur simultaneously. Alternatively, the second recombination event can occur as a condensation event. It is contemplated that the portion of the target nucleic acid from the plasmid inserted into the bacteriophage may be modified. For example, it may include selectable markers, insertions, mutations, deletions etc.

For recombination between the bacteriophage and the plasmid the target nucleic acid sequences on the plasmid and bacteriophage are substantially homologous. Preferably the percentage of homology between the two sequences is at least about 80%, more preferably it is at least about 90% and most preferably it is at least about 95%. One hundred percent sequence homology is most preferred. A practical lower limit to sequence homology can be defined as that amount of homology which if further reduced does not mediate homologous integration of the plasmid with the bacteriophage. Although as few as 25 bp of 100% homology are required for homologous recombination in prokaryotic cells, longer regions are preferred. The region of substantial homology is preferably at least about 500 bp, more preferably at least about 1 kb and most preferably at least about 2 kb in total length. If non-homology does exist between the homologous portions of the vector and the target nucleic acid, it is preferred that the non-homology not be spread throughout the homologous portion but rather be in discrete areas.

It is contemplated that the bacteriophage may contain a reporter gene. The term "reporter gene" refers to a gene which encodes for a protein product that is readily detectable in the transformed target cell. Examples of such "reporter genes" include lacZ, gfp (green fluorescent protein) and cat (chloramphenicol acetyl transferase).

The term "transformed eukaryotic target cells" refer to those eukaryotic target cells wherein the targeting vector has undergone homologous integration into the cells genome.

The term "assortment of bacteriophage" or collection of bacteriophage" refers to a library or bank of bacteriophage in which each bacteriophage is similar except each comprises a different heterologous nucleic acid sequence, usually from the eukaryotic genome. Such assortments may comprise at least about $5\times10^5$ to about $10^7$ different bacteriophage.

Methodology

The present invention relates to the generation of λ and P1 bacteriophage comprising a target nucleic acid sequence.

Bacteriophage/plasmid recombination may be used to direct modified target nucleic acid sequences from plasmids into specific target nucleic acid sites within bacteriophage vectors, without the use of restriction enzymes. Bacteriophage vectors generated by bacteriophage/plasmid recombination may result in either single or double-crossover recombinants. The present invention is directed to a method for selecting for double-crossover recombinants. The resulting bacteriophage targeting vector can be transfected directly into eukaryotic cells as a bacteriophage particle to yield modified eukaryotic cells. Alternatively the vector nucleic acid can be isolated and electroporated into cells. Finally, the targeting vector nucleic acid may be cleaved with restriction endonucleases to release the bacteriophage arms and the resulting modified target nucleic acid sequence can be transfected directly into eukaryotic cells.

The method of this invention may also be used to insert modified target nucleic acid sequences into the target nucleic acid sequence in bacteriophage and select for the recombinant bacteriophage. This allows the deposition of a mutation, insertion, deletion, substitution or alteration into a larger target nucleic acid sequence without restriction enzyme digestion.

Finally, the method of this invention may be used to screen a bacteriophage library to select recombinant bacteriophage comprising the desired target nucleic acid sequence from an assortment of bacteriophage.

Figure 1B:
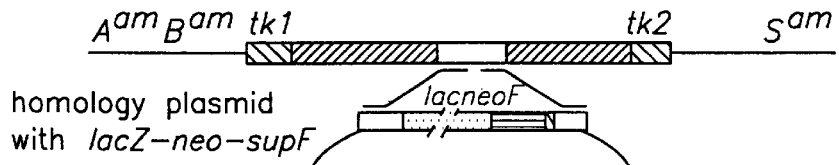
FIG. 1B illustrates a double-crossover recombination event with a lacz-neo-supF ("lacneoF") split homology bearing plasmid.

FIGS. 1A and 1B show the methods of generating the targeting bacteriophage vectors by single or double-crossover phage/plasmid recombination. In FIG. 1A the original bacteriophage vector contains the target nucleic acid sequences (open boxes) with the nucleic acid sequence encoding the negative eukaryotic selectable markers, in this case TK1 and TK2, located 5' and 3' to the target nucleic acid sequence. The plasmid contains a target nucleic acid sequence (open boxes) with the nucleic acid sequence encoding the positive eukaryotic selectable marker, ie. neo and the positive prokaryotic selectable marker supF (F), positioned within the target nucleic acid sequence. The plasmid also contains the recombination selectable marker, ie. gam, 3' to the target nucleic acid sequence.

The bacteriophage is allowed to infect bacterial cells having the plasmid under lytic conditions such that homologous recombination between the target nucleic acid sequence present on the bacteriophage and the plasmid occurs. When a single-crossover event occurs (2), the entire plasmid is inserted into the bacteriophage between the two copies of the target nucleic acid sequence. Where double-crossover recombination occurs (1), the plasmid nucleic acid will not be inserted into the bacteriophage. The resulting bacteriophage targeting vector will contain the positive eukaryotic and prokaryotic selectable markers but will not include the recombination selectable marker gene gam.

In this example, double-crossover bacteriophage targeting vectors can be selected by their ability to replicate lytically on P2 lysogenic $sup^0$ cells. On the other hand, after a single crossover, the gam gene will also be present in the bacteriophage and accordingly, the bacteriophage will not be able to replicate in a lytic pathway on P2 lysogenic $sup^0$ cells but instead will undergo lysogeny.

In FIG. 1B the first bacteriophage vector contains the target nucleic acid sequences with the nucleic acid sequence encoding the negative selectable marker, in this case TK1 and TK2 located 5' and 3' to the target sequence. The plasmid contains a target nucleic acid sequence with the third nucleic acid sequence encoding the positive eukaryotic and prokaryotic selectable markers, ie. lacneoF, positioned within the target nucleic acid sequence. When single-crossover recombination occurs, the entire plasmid is inserted into the bacteriophage target nucleic acid sequence. Such a construct is too large to be packaged into a bacteriophage virion. Where double-crossover recombination occurs, the resulting bacteriophage will contain the positive selectable markers inserted within the target nucleic acid sequence. The size of the bacteriophage nucleic acid will be smaller than that produced by a single cross-over event which will allow it to be packaged.

In this example, double-crossover recombination can be selected where the bacteriophage particle or head has limitations on the size of nucleic acid which can be incorporated into it. Because of the size of bacteriophage nucleic acid resulting from a double-crossover recombination, such bacteriophage nucleic acid will be exclusively packaged into the bacteriophage particle in the host cell. The bacteriophage nucleic acid resulting from single-crossover recombination can not be packaged and, accordingly, will not form viable bacteriophage in the host cell.

Other methods which specifically select for double-crossover events are contemplated, for example utilization of negative markers such as P2 old (19) and λred (18).

Using phage-plasmid recombination to generate the targeting vector confers the advantage that unique restriction enzyme sites do not need to be identified in the first and second targeting nucleic acid sequences to enable insertion of the positive selectable marker or alternatively the insertion of a modified target nucleic acid sequence.

It is contemplated that the bacteriophage may further comprises sequences for the transcription and translation of the target nucleic acid sequence, for example, enhancers, promoters and signal sequences.

The plasmids may be generated using conventional restriction enzyme digestion and ligation. The target nucleic acid sequence is identified, digested with the appropriate restriction enzyme and inserted into the plasmid at an appropriate restriction enzyme site through ligation. The target nucleic acid sequence may also be generated synthetically using methods known in the art.

The plasmid can be any plasmid capable of recombination with a λ or P1 bacteriophage. Preferably the bacteriophage is pBluescript (Stratagene, La Jolla Calif.), πAN13 or πOCT.

The positive prokaryotic selectable marker, the positive eukaryotic selectable marker and the double-crossover selectable marker are all inserted into the plasmid using conventional restriction enzyme digestion and ligation.

The modified target nucleic acid sequence may be generated using conventional methods. Oligonucleotides having the desired modification can be synthesized and inserted into the plasmid through conventional restriction enzyme digestion and ligation. Substitutions, deletions, insertions or any combination thereof may be introduced or combined to arrive at a final construct. Nucleic acid substitutions are typically introduced for single residues and deletions will range from about one to about thirty residues.

Insertional nucleotide sequence variants of the target nucleic acid are those in which one or more nucleotide residues extraneous to the target nucleic acid are introduced into a predetermined site in the target nucleic acid and which displace the pre-existing nucleotide residues. Commonly, insertional variants are fusions of heterologous genes to the target nucleic acid.

Substitutional variants are those in which at least one nucleotide residue in the target nucleic acid sequence has been removed and a different nucleotide inserted in its place.

Some deletions, insertions and substitutions will not produce radical changes in the characteristics of the target nucleic acid. However, while it is difficult to predict the exact effect of the substitution, deletion or insertion in advance of doing so, one skilled in the art will appreciate that the effect will be evaluated by routine screening assays.

It is contemplated that libraries or assortments of bacteriophage can be generated which bacteriophage comprise a variety of large genomic fragments or putative target nucleic acid sequences. Recombination can be used to both insert a positive selectable marker into the desired target nucleic acid and to select the particular bacteriophage vector containing the desired target nucleic acid from the library.

Such a library may be passaged in a bacterial cell line comprising a plasmid containing a positive prokaryotic selectable marker 5', 3' or within the desired target nucleic acid under conditions whereby the plasmid nucleic acid recombines with the bacteriophage nucleic acid producing recombinant bacteriophage nucleic acid containing the positive prokaryotic selectable marker. Only those bacteriophage bearing nucleic acid sequences homologous to the desired target nucleic acid sequence will recombine with the plasmid thereby identifying a particular bacteriophage having the desired target nucleic acid sequence.

Figure 6A:
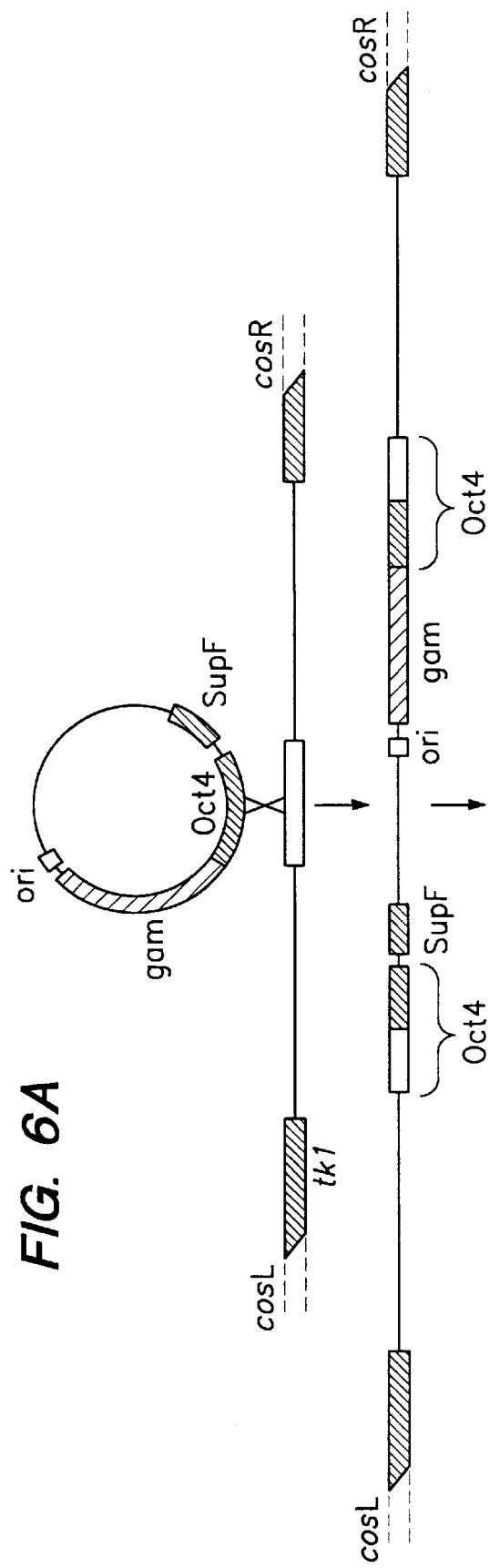
FIG. 6A illustrates a single-crossover recombination event between the λTK bacteriophage vector and the plasmid πOCTγ.
Figure 6B:
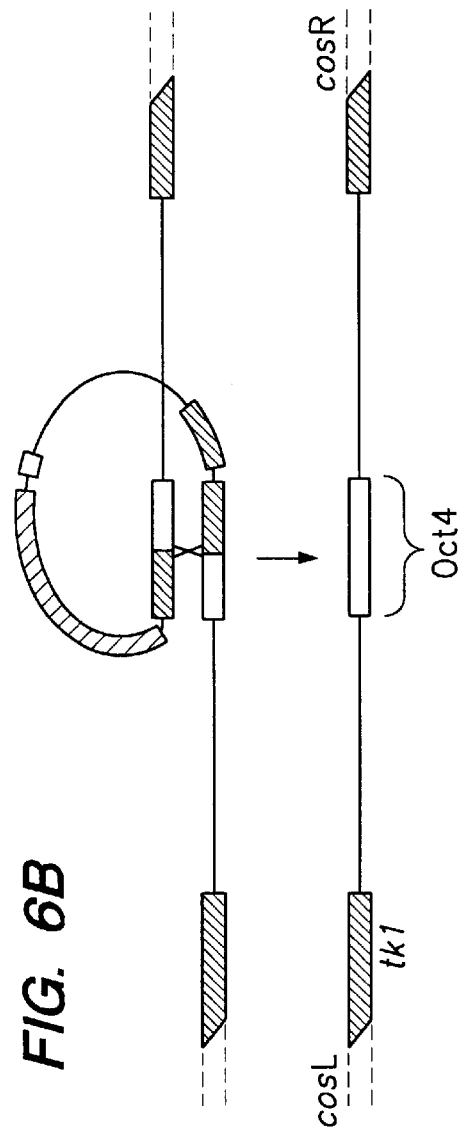
FIG. 6B shows a condensation event after the recombination between the λTK bacteriophage vector and the plasmid πOCTγ resulting in a double-crossover recombinant.

With reference to FIGS. 6A and 6B, the positive prokaryotic selectable marker SupF is located on the plasmid 3' to the target nucleic acid Oct4 gene. Homologous single-crossover recombination between the plasmid and a bacteriophage having the Oct4 gene inserts the entire plasmid genome into the Oct4 gene on the bacteriophage. Bacteriophage having undergone recombination have acquired SupF and thus are able replicate. The bacteriophage is then grown under relaxed conditions such that the bacteriophage does not require the SupF gene to replicate. This allows condensation of the bacteriophage, i.e. the second crossover recombination. See FIG. 6B. The bacteriophage are subsequently passaged through a P2 lysogenic bacteria which selects for bacteriophage which have undergone double-crossover recombination removing the plasmid sequences, including the gam gene.

In general the bacteriophage targeting vector has a total length of between 20 kb and 300 kb, more preferably between 40 kb and 150 kb.

Once the recombinant bacteriophage has been generated, the intact recombinant bacteriophage may be introduced directly into the eukaryotic cell for gene targeting by electroporation, calcium phosphate precipitation, lipid mediated transfections and receptor or epitope mediated systems. Calcium phosphate precipitation has previously been successfully used to introduce λ phage into mammalian cells. Currently, lipid reagents such as Lipofectin™ are used to deliver naked DNA to mammalian cells. It is contemplated that lipid reagents could be used to deliver bacteriophage particles to eukaryotic cells. It further is contemplated that a cell surface epitope library may be developed in λ phage in order to identify epitopes that permit the interaction of λ on the ES cell surface or other target cell surfaces. A epitope library system has been generated in λ bacteriophage (28).

It is contemplated that the nucleic acid may be isolated from the bacteriophage before introduction of the bacteriophage nucleic acid into the target cell. The recombinant phage nucleic acid may be removed from the phage particle by methods known in the art including chelating the DNA out of the particle with magnesium ions in the presence of EDTA and sodium dodecyl sulfate (SDS) or by heating the phage in the presence of EDTA and SDS and then denaturing the protein with phenol/chloroform. The DNA can then be transfected into the eukaryotic target cells by electroporation, calcium phosphate precipitation and lipid mediated transfections. Currently, lipid reagents such as Lipofectin® are used to deliver naked DNA to mammalian cells. It is further contemplated that the bacteriophage DNA arms may be removed through restriction enzyme digestion prior to introduction of the modifying target nucleic acid sequence into the target cell.

For recombination between the target nucleic acid sequence in the bacteriophage and the target nucleic acid in the eukaryotic cell, the target nucleic acid sequences on the bacteriophage and in the eukaryotic cell are substantially homologous. The sequences are substantially homologous for eukaryotic recombination when the homology is at least about 90%, most preferably it is at least about 95% and most preferably it is at least about 98%. One hundred percent sequence homology is most preferred for eukaryotic recombination. A practical lower limit to sequence homology can be defined as that amount of homology which if further reduced does not mediate homologous integration of the bacteriophage target nucleic acid sequence into the genome of the eukaryotic cell. Longer regions of substantial homology are preferred. The region of substantial homology is preferably at least about 500 bp, more preferably at least about 3 kb and most preferably at least about 10 kb in total length for the target nucleic acid sequences. If non-homology does exist between the homologous portions of the vector and the target nucleic acid, it is preferred that the non-homology not be spread throughout the homologous portion but rather in discrete areas of the homologous portion.

The gene targeting may be practiced with any cell type which is capable of homologous recombination. Examples of such target cells include cells derived from vertebrates including mammals such as humans, bovine species, ovine species, murine species, simian species; other eukaryotic organisms such as fungi and higher multicellular organisms such as plants.

In those cases where the ultimate goal is the production of a non-human transgenic animal, embryonic stem cells (ES cells) are preferred target cells. Such cells have been manipulated to introduce transgenes. ES cells are obtained from pre-implantation embryos cultured in vitro. Another preferred source of cells are primordial germ cells or embryonic germ cells (EG cells). It is also contemplated that mammary epithelial cells may be used as target cells. Once the mammary epithelial cell has been transformed, the nucleus of the cell may be introduced into a oocyte to give rise to a transgenic animal by methods known in the art.

Targeting vectors can be introduced into ES cells by electroporation or microinjection or other transformation methods, preferably electroporation. Such transformed ES cells can thereafter be combined with blastocytes from a mammal. The ES cells thereafter colonize the embryo and can contribute to the germ line resulting in a chimeric animal.

Where the ultimate goal is gene therapy to correct a genetic defect in an organism such as a human being, the cell type will be determined by the etiology of the particular disease and how it is manifested. For example, hemopoietic stem cells are a preferred cell for correcting genetic disorders in cell types which differentiate from such stem cells, e.g. erythrocytes and leukocytes. Other types of stem cells include epithelial, liver, lung muscle, endothelial, menchymal, neural and bone stem cells.

Alternatively, certain disease states can be treated by modifying the genome of cells in a way which does not correct a genetic defect per se but provides for the supplementation of the gene product of a defective gene. For example, endothelial cells are preferred as targets for human gene therapy to treat disorders affecting factors normally present in the systemic circulation. Since endothelial cells form an integral part of the graft, such transformed cells can be used to produce proteins to be secreted into the circulatory system and thus serve as therapeutic agents in the treatment of genetic disorders affecting circulating factors. Examples of such diseases include insulin-deficient diabetes, α-1-antitrypsin deficiency, and hemophilia.

Utility

The vectors generated by the methods of the present invention are useful for gene targeting and gene expression studies. The vectors may be used to transform various mammalian cells. As indicated, genetic defects may be corrected in specific cell lines by transforming the cell lines with the targeting vector, wherein the positive selectable marker is positioned in an untranslated region such as an intron near the site of the genetic defect together with flanking sequences to correct the defect or to generate the defect.

Described herein are methods for the construction of vectors without the need to isolate, analyze, manipulate or otherwise characterize the genomic target nucleic acid sequence. These methods are useful for generating point mutations or other modifications of the target nucleic acid sequence without having to use restriction endonucleases or polymerases. Therefore, the methods set forth herein shorten the time needed to construct such vectors. Furthermore, the bacteriophage are capable of stably containing large fragments of target nucleic acid sequences.

Also provided are methods useful for isolating specific bacteriophage from an assortment of bacteriophage or a library without hybridizations. The methods of this invention are useful for the identification of larger genomic target nucleic acid sequences in bacteriophage through the use of smaller target nucleic acid sequences present on plasmids. In particular this method is useful in isolating bacteriophage having large genomic fragments with small target nucleic acid sequences or ESTs randomly isolated from the human genome and cloned into plasmids. Such a method provides for the identification of specific bacteriophage with high fidelity. Once recombinant bacteriophage have been identified, it is contemplated that they can subsequently be used in gene targeting again without further cloning or the need to characterize the nucleic acid sequence.

The bacteriophage particles are useful for gene targeting. Electroporation of the particles into eukaryotic cells results in transfer of the target nucleic acid sequence into the eukaryotic cell.

The vectors and methods of the invention are also applicable to the manipulation of plant cells and ultimately the genome of the entire plant. A wide variety of transgenic plants have been reported, including herbaceous dicots, woody dicots and monocots. A number of different gene transfer techniques have been developed for producing such transgenic plants and transformed plant cells.

As can be appreciated from the disclosure above, the present invention has a wide variety of applications. Accordingly, the following examples are offered by way of illustration and not by way of limitation.

EXAMPLES

In the examples below, the following abbreviations have the following meanings. If not defined below, then the abbreviations have their art recognized meanings.

| TV | targeting vector |
|---|---|
| ES cells | embryonic stem cells |
| kb | kilobase |
| bp | base pairs |
| ml | milliliters |
| µl | microliters |
| neo | neomycin gene |
| supF | suppressor F gene (amber suppressor tRNA gene) |
| spi | Sensitive to P2 Interference phenotype |
| gam | λ gamma gene encodes spi+ phenotype |
| Rap | recombination adept with plasmid |
| λ | lambda bacteriophage |
| EDTA | ethylene diamine tetra-acetic acid |
| SDS | sodium dodecyl sulfate |
| LIF | leukemia inhibitory factor |
| tk | thymidine kinase |
| HSV | herpes simplex virus |
| r | resistant |
| am | amber mutation |
| pfu | plaque forming units |
| PBS | phosphate buffered saline |
| FIAU | 1-[2'-deoxy-2'-fluoro-1-beta-D-arabinofuranosyl]-5-iodo-uridine |

EXAMPLE 1

Phage-Plasmid Recombination and Selection for Double-crossover Recombinants

Two strategies were tested to see whether double-crossover events could be enriched by eliminating single crossover phage (FIG. 1). In the first approach, a spi selection system was devised to eliminate phage that have integrated the entire recombination plasmid (FIG. 1A). λ phage that carry a functional copy of the gam gene are Sensitive to P2 Interference (spi$^+$) and cannot be replicated on a P2 lysogenic host (18, 19). Thus, if gam function could be maintained in a recombination plasmid, single crossover integrants bearing gam could be eliminated on a P2 lysogen. This approach was used to make a neo-containing targeting vector. The second strategy took advantage of the size limitation in packaging λ phage (23; FIG. 1B). Thus, if a relatively large recombination plasmid was used in the reaction, only double-crossover phage could be propagated following recombination. This approach was used to make a lacZ-neo targeting vector.

*E. coli* strain MC1061 (rec$^+$, sup$^0$), its P2 lysogenic derivative P2MC1061, as well as MC1061[P3] were kindly provided by Dr. D. M. Kurnit (University of Michigan, Ann Arbor, Mich.). *E. coli* strain LE392 (rec$^+$, supE, supF) and its P2 lysogenic derivative P2392 were obtained from Stratagene (La Jolla, Calif.).

For routine cloning in phage, λ packaging extracts (Amersham, Oakville Ontario Canada) were split into thirds and either used directly or refrozen on dry ice for later use.

Figures 2A, 2B, 2C:
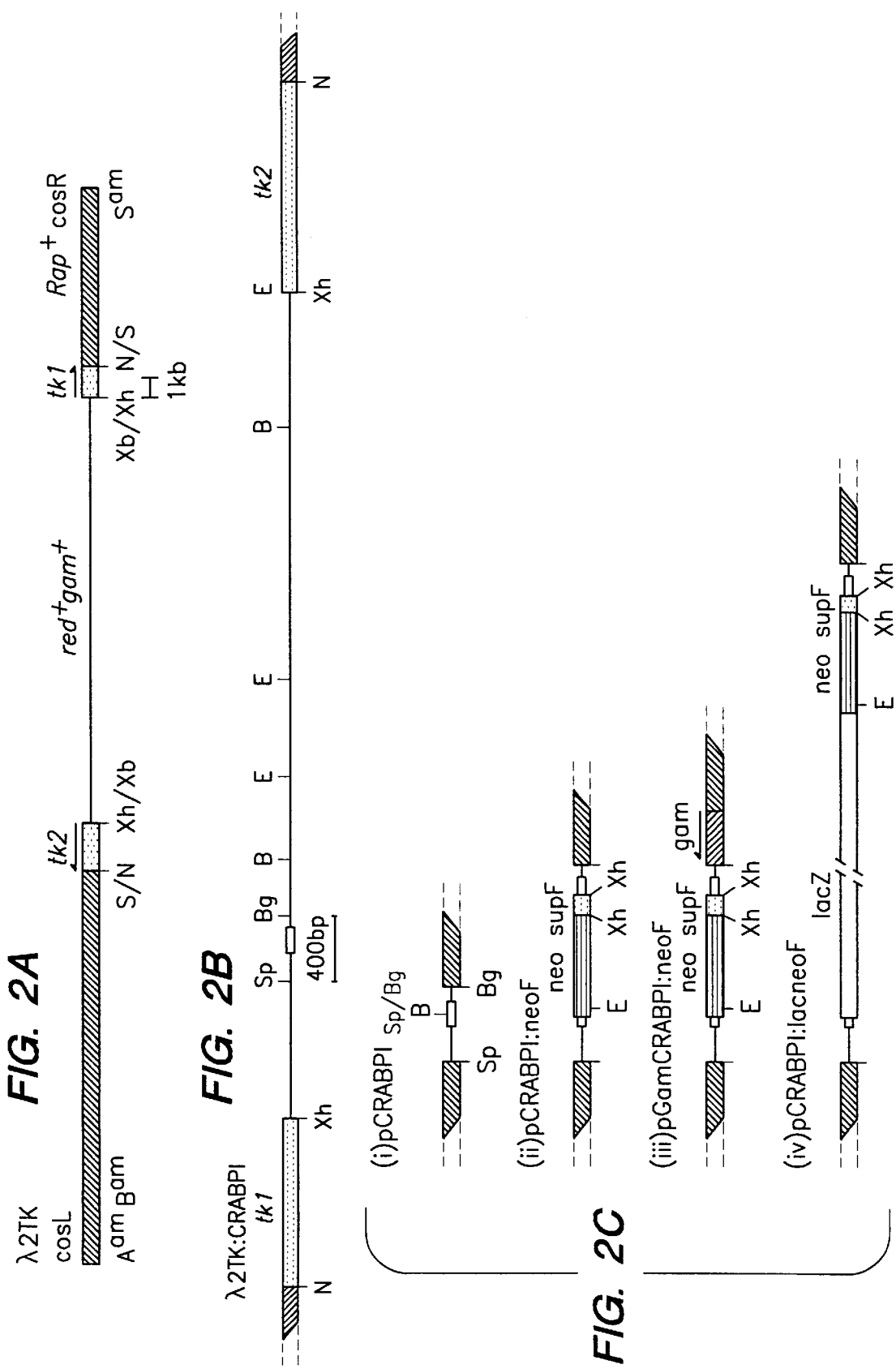
FIG. 2A shows the restriction enzyme map for the λ2TK. Restriction sites for cloning (Xh=XhoI; Xb=XbaI) or for excising arms (S=SalI; N=NotI) are shown.
FIG. 2B shows the restriction enzyme map for λ2TK:CRABPI. The position of the 400 bp SpeI–BglII fragment encompassing the region of homology used in the homologous recombination experiments is indicated.
FIG. 2C shows the restriction enzyme maps for pCRABPI$_{Sp/Bg}$; pCRABPI:neoF; pGamCRABPI:neoF and pCRABPI:lacneoF. The SstI site in pCRABPI$_{Sp/Bg}$ has been converted to BamHI for the introduction of neo-supF or lacZ-neo-supF.

The gene targeting bacteriophage vector λ2TK (FIG. 2A) was preceded by the construction of a λDash II (Stratagene, La Jolla Calif.) derivative. Thymidine kinase genes from Herpes simplex virus 1 and 2 (HSVtk1 and tk2; 11, 14) were inserted into the left and right polylinkers of λDash II respectively, between the NotI and XhoI sites. A SalI fragment comprising the two tk genes and stuffer region was then transferred into λSyrinx2A (15) (ATCC No. 37543) to place the tk1 and tk2 genes adjacent to the short and long arms of the phage, respectively. Finally, an XhoI fragment containing the polylinker and stuffer region of λGem11 (Promega, Madison Wis.) was shuffled into this derivative to yield λ2TK (FIG. 2).

The λ2TK vector has a gam$^+$ stuffer fragment to enable spi$^-$ selection of cloned inserts (18); and HSV-tk1 and tk2 genes adjacent to its small and large arms, respectively. The tk1 and tk2 genes serve as negative selectable makers in gene targeting experiments (11). Otherwise, as with λSyrinx2A, λ2TK is A$^{am}$, B$^{am}$, S$^{am}$, requires the amber suppressor tRNA, supF, for lytic growth and is Rap$^+$ for efficient recombination with plasmid. The vector has unique XbaI and XhoI restriction sites for the subcloning of relatively longer genomic pieces and can receive fragments ranging in size from 3.5 to 16.5 kb. Since the XbaI is compatible with SpeI and AvrII while XhoI can accommodate SalI, in addition to BamHI, BglII, BclI, Sau3A by partial fill-in of cohesive ends, there is a considerable amount of flexibility in the subcloning of genomic regions. Following the construction of a targeting vector, the phage arms can be excised with the rare cutting enzymes SalI or NotI for direct electroporation into ES cells.

The gene for cellular retinoic acid binding protein I (cRABPI), which has been previously disrupted in mice (24) was used as a model. The bacteriophage vector used for plasmid-phage recombination, λ2TK:CRABPI (FIG. 2B) was generated by inserting into λ2TK, a 9.5 kb XhoI fragment encompassing the second and third exons of the murine cellular retinoic acid binding protein I gene (cRABPI) (16) which was isolated from a murine genomic library.

All of the plasmid constructs used in this study were harbored in the E. coli rec+ host MC1061. Plasmids bearing the supF gene were harbored in E. coli MC1061[P3]. The P3 episome which is $Kan^r$, $Amp^{am}$, $Tet^{am}$ facilitates the selection of supF in media containing kanamycin, ampicillin and tetracycline (17). However, the $Amp^{am}$ and $Tet^{am}$ genes are functional only if SupF activity is provided in trans. Since all of the plasmids used in this Example were ampicillin resistant, only tetracycline served to functionally select for the presence of supF.

The plasmid pGam was generated by excising a 500bp Sal I fragment containing the gam gene coding sequence from bacteriophage λ (18) and inserting it into the SalI site of pBluescriptKS+(Stratagene, La Jolla Calif.). spi+ (Sensitive to P2 Interference) activity (18; 19) conferred by pGam was assessed initially by its inability to be grown in red−, gam− recombinant λ phage plated on E. coli P2392.

The construction of the recombination plasmids used in this study (FIG. 2C) was preceded by the assembly of $pCRABPI_{Bg/sp}$ which is a small 400bp BglII-SpeI genomic subclone that encompasses the second exon of cRABPI. An SstI site which bisects this genomic fragment was converted to BamHI in order to facilitate the cloning of supF-bearing cassettes of MClneopA (4) and lacz-MClneopA (5) in pCRABPI:neoF and pCRABPI:lacneoF, respectively. See FIG. 3B.

For the recombination strategy which utilized λgam and spi selection to eliminate single crossover phage, the homology and neoF regions were subcloned in pGam to generate pGamCRABPI:neoF (FIG. 2C). pGam is a pBluescript derivative that carries a functional λgam gene and can confer a spi+ phenotype to recombinant phage.

For the strategy involving size limitation of λ packaging, pCRABPI:lacneoF (FIG. 2C) was constructed, which placed a lacZ-neo-supF cassette in frame within $pCRABPI_{Sp/Bg}$. As this plasmid was 8.7 kb in length, it was theoretically too large to integrate into the vector by single crossover. The 5.7 kb lacZ-neo-supF portion, however, was sufficiently small to be converted into the λ2TK:CRABPI targeting vector by double-crossover.

λ2TK:CRABPI phage ($1 \times 10^3$ pfu) were passaged via plate lysates over LE392 or MC1061[P3] E. coli cells, bearing pCRABPI:neoF, pGamCRABPI:neoF or pCRABPI:lacZneoF overnight at 37° C. The supernatant phage were collected the following day in phage dilution buffer and used to infect the supF+ control strain LE392 in order to estimate the titer of harvested phage and the indicator strain restrictive host MC1061 E. coli cells to evaluate the titer of supF+ recombinant phage. In addition, to confirm gam gene function in pGamCRABPI:neoF, the supernatants were plated on a P2 lysogen of MC1061 E. coli cells. As shown in Table II, the passage of λ2TK:CRABPI through LE392 resulted in no detectable supF+ phage in $10^6$ that were plated. In contrast, phage passaged through strains bearing the recombination plasmids did result in supF+ recombinants, albeit at differing frequencies.

TABLE II

Frequency of Phage-Plasmid Recombinations

| Original Passage | Recombination Frequencies | |
|---|---|---|
| | MC1061 | P2MC1061 |
| LE392 | 0 | 0 |
| MC1061[P3,pCRABPI:neoF] | $7.1 \times 10^{-2}$ | $7.1 \times 10^{-2}$ |
| MC1061[P3,pGamCRABPI:neoF] | $2.5 \times 10^{-2}$ | $3.4 \times 10^{-3}$ |
| MC1061[P3,pCRABPI:lacneoF] | $5.1 \times 10^{-5}$ | $5.1 \times 10^{-5}$ |

Recombination frequencies represent: titer of phage on the restrictive host/titer of phage on LE392

Passage through MC1061[P3, pCRABPI:neoF] resulted in roughly 7% recombinants as indicated by supF+ phage grown on MC1061. Passage through MC1061 [P3, pGamCRABPI: neoF] resulted in ~60% fewer recombinants suggesting that the gam gene perturbed recombination to some extent. Ten percent of these recombinants could grow on P2MC1061 which indicated that spi selection could functionally select against single crossover phage and that the frequency of double-crossover phage was approximately $3 \times 10^{-3}$. Similarly, double-crossover recombinants resulting from the passage of λ2TK:CRABPI through MC1061 [P3, pCRABPI:lacneoF] occurred at a frequency of $\sim 5 \times 10^{-5}$. This number was found to be the same when plated on MC1061 and P2MC1061 indicating that, as with pCRABPI:neoF, the P2 lysogen did not affect the plating efficiency of recombinants not carrying the gam gene. Interestingly, when the distance between the homologous sequence was increased from 1.4 to 5.7 kb, the frequency of double-crossover recombination dropped by almost two orders of magnitude. This is different from what is observed in gene targeting of mammalian cells where insert size appears to have little influence on gene targeting frequency.

Figure 3A:
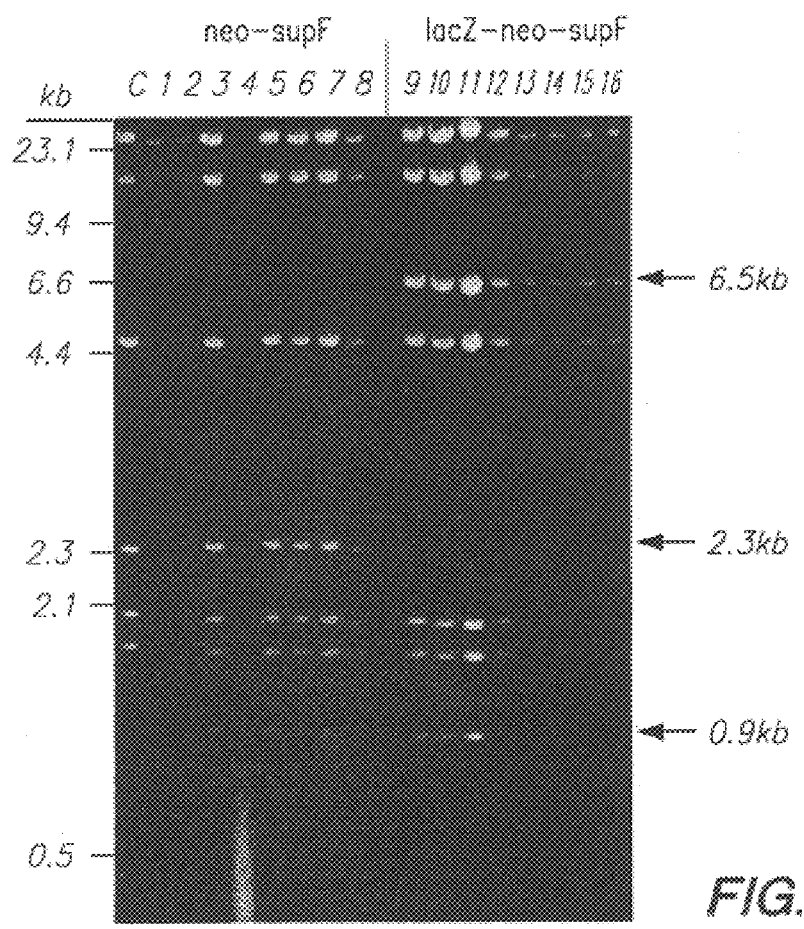
FIG. 3A is a photograph of an agarose gel stained with ethidium bromide, showing the DNAs from λ2TK:CRABPI (lane C), putative neo-supF (lanes 1–8) and lacZ-neo-supF (lanes 9–16) after digestion with BamHI and XhoI. The migration distances of DNA standards are shown on the left.
Figure 3B:
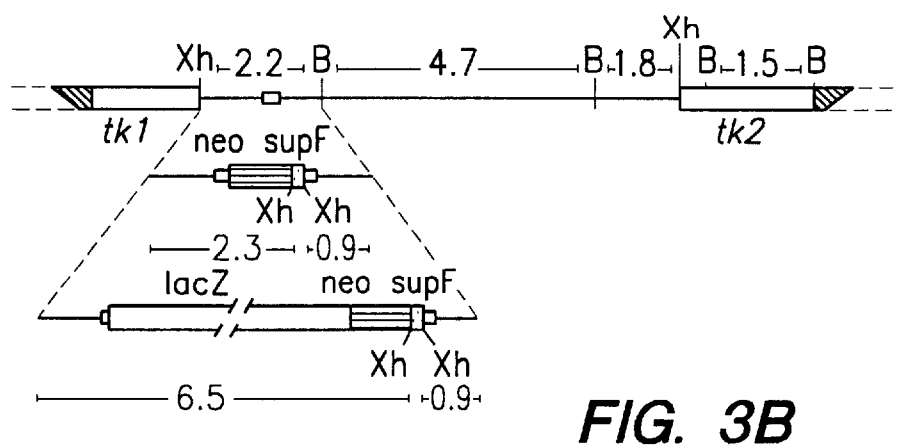
FIG. 3B is a restriction map of λ2TK:CRABPI and the molecular weight of the corresponding fragments is indicated. Fragments resulting from the integration of neo-supF or lacZ-neo-supF are shown underneath.

To establish the authenticity of the apparent double-crossover recombinants in both experiments, individual plaques were isolated from the P2MC1061 plates and phage were grown in small scale. DNAs from putative recombinants were digested with BamHI and XhoI, separated on a 0.5% agarose gel and stained with ethidium bromide. Restriction analysis of 15 phage clones using BamHI and XhoI indicated that in all cases a double-crossover had indeed occurred (FIG. 3A). In FIG. 3A, the migration distances of DNA standards derived from a HindII digest of λ DNA are shown in the left. Shifted bands due to double-crossover recombination are indicated on the right.

For neo-supF, the 2.2 kb XhoI-BamHI fragment from λ2TK:CRABPI is present as two bands as a result of the XhoI sites flanking the supF gene. The 5' fragment which contains the neo gene is 2.3 kb in length, while the 3' fragment has been shifted down to 0.9 kb. Similarly, for lacZ-neo-supF, the 2.2 kb parental fragment is shifted to two bands, however, in this case the 5' fragment is shifted up to 6.5 kb as a result of the large lacZ-neo insertion, while the 3' fragment (0.9 kb) is common in both the cRABPI:neoF and cRABPI:lacneoF targeting vectors. The other common fragments: 4.7 kb, 1.8 kb and 1.5 kb lie outside the recombination site and are common to λ2TK:CRABPI and its neoF and lacneoF derivatives.

This illustrates that flanking homologous sequences as short as 200 bp are sufficient to introduce heterologous sequences ranging from 1.4–5.7 kb into phage. It has further been discovered that flanking homologous sequences derived from oligonucleotides as short as 25 bp are sufficient to direct double-crossover recombination of neo-supF cassettes in phage targeting vectors, albeit at a lower frequency of $10^{-7}$.

EXAMPLE 2

Gene Targeting

Phage targeting vectors were introduced into ES cells by electroporation, by methods previously described for plasmid targeting vectors (4). Prior to electroporation, the arms of the λ targeting vector were removed by digestion with NotI and the DNA concentration was estimated on the basis of insert only. Targeted cell lines were enriched by positive-negative selection (11) using FIAU (1-[2'-deoxy-2'-fluoro-1-beta-D-arabinofuranosyl]-5-iodo-uridine) instead of gancyclovir for negative selection (20). Clones bearing targeting events were identified by genomic Southern blotting using a probe which flanked the 5' end of the targeting vector (4). Integrity of the targeted locus was confirmed using a probe internal to the locus which spanned the site of the neomycin gene insertion.

To demonstrate that phage vectors could be used successfully in gene targeting experiments, double-crossover clones bearing neo (λ2TK:CRABPI:neoF) and lacZ-neo (λ2TK:CRABPI:lacneoF) were grown in large scale and prepared for electroporation into ES cells by excising the phage arms with NotI or SalI. Following electroporation, ES cells were grown in media containing G418 and FIAU (4, 20).

Figure 4A:
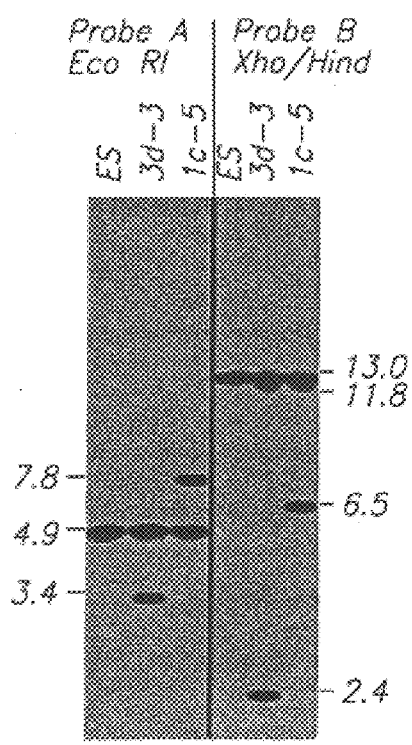
FIG. 4A is a photograph of a Southern blot of genomic DNAs from parental (ES) a neo-targeted (3d-3) and a lacZ-neo-targeted (1c-5) cell line digested with EcoRI or XhoI-HindIII. The genomic DNA was hybridized with probes A or B. Molecular weights of the hybridizing fragments are indicated.

For λ2TK:CRABPI:neoF, 7 out of 96 cell lines had neo integrated within the cRABPI locus, while for λ2TK:CRABPI:lacneoF, 3 out of 40 were positively targeted. Southern blot analysis of representative cell lines is shown in FIG. 4A.

Figure 4B:
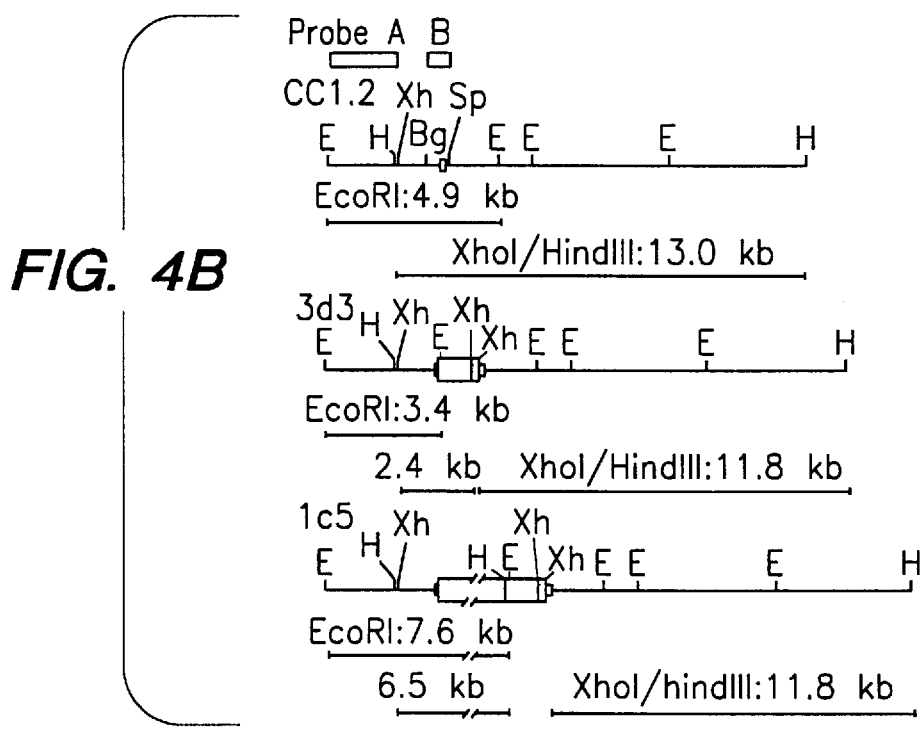
FIG. 4B illustrates the restriction map of the cRABPI locus in parental (CC1.2) and targeted cell lines (3d3 and 1c5). The size of the hybridizing bands from each digest are shown and the positions of probes A and B are indicated.

Individual clones resistant to both drugs were subjected to genomic Southern blotting analysis. Genomic DNAs from parental (CC1.2) a neo-targeted (3d3) and a lacZ-neo-targeted (1c5) cell line were digested with EcoRI (Probe A) or XhoI–HindII (Probe B) and blotted onto nylon filters and hybridized with corresponding probes. Molecular weights of the hybridizing fragments are indicated in FIG. 4A. The restriction maps of the cRABPI locus in parental and targeted cells lines is indicated in FIG. 4B, as are the sizes of the hybridizing bands in each digest. The positions of the flanking probe A and internal probe B are also indicated.

Parental ES cell DNA digested with EcoRI and hybridized with the 5'-flanking probe A yielded a 4.9 kb fragment. In cell lines targeted with neo (3d3), a portion of this hybridizing band representing the targeted locus was shifted down to 3.4 kb due to the presence of an EcoRI site in the neo gene cassette. With the lacZ-neo targets (1c5), this hybridizing band shifted up to 7.8 kb because of lacZ sequences upstream of the EcoRI site in neo.

In addition to detecting targeted cell lines, analysis with EcoRI and probe A confirmed the integrity of the 5' end of the targeted locus. To confirm that the 3' end of each target was intact, DNAs from parental and targeted cell lines were digested with XhoI plus HindIII and probed with the internal SpeI-BglII fragment (Probe B). In parental DNA, digestion with XhoI and HindIII resulted in a 13 kb fragment which spanned the targeted region beyond the 3' end of the targeting vector. In both targeted cell lines (3d3 and 1c5), this fragment shifted to a lower molecular weight due to the presence of XhoI sites flanking the supF gene at the 3' end of both the neo and lacZ-neo insertions. On the 3' end, an 11.8 kb fragment resulted which was common to both the neo and lacZ-neo targeted cell lines. At the 5' end, a 2.4 kb band in the neo target contained the 5' end of this fragment plus neo. In the lacZ-neo target, a 6.5 kb fragment contained only the lacZ gene due to the presence of a HindIII site separating lacZ and neo.

EXAMPLE 3

Bacteriophage mediated targeting vector delivery into ES cells

In general when electroporation is used to deliver DNA into cells it breaks the DNA as it forces it into the cells. DNA breakage constitutes a major problem for gene targeting efficiencies in two ways. First breakage within critical homology regions of the targeting vector can seriously affect the ability of the targeting vector to undergo targeted replacement. Second, negative selectable markers (i.e. HSV-TK) are severed from the end(s) of the gene targeting vector, allowing many random integrants to survive positive-negative selection. Indeed, as much as 99% of cells surviving positive-negative selection are random integrants bearing broken or missing HSV-TK genes. In gene targeting, it is often difficult to find a targeted integration amongst a sea of random integrants surviving positive-negative selection.

In order to avoid the DNA breakage of electroporation, intact recombinant bacteriophage targeting vectors were delivered to ES cells directly by electroporation.

The λ2TK:cRABPI:lacZneoF targeting vector phage particles were purified via a cesium chloride density gradient. The isolated phage band was dialysed in TM buffer (50 mM Tris, 10 mM $MgCl_2$ (pH 7.5) with several changes to remove the CsCl. The phage was diluted to $10^{11}$ pfu (approx. 5 μg of DNA) of phage in 1 ml of TM buffer and dialyzed against cold PBS containing 10 mmol $MgCl_2$ for 6 hours. The phage was then passaged through a 0.45 μM filter and kept on ice.

Three plates of ES cells (~$10^7$ cells/dish) were trypsinized together in 1 ml of trypsin and then 1 ml of perfect pH medium/dish was added. The cells were collected into a 15 ml conical tube and broken into single cells using a pipette. The cells were preplated for 30 minutes to allow feeders to attach and then the ES cells were thoroughly rinsed off into a 50 ml conical tube. Approximately $7 \times 10^6$ cells were centrifuged (270 g, 5 minutes).

The media was aspirated and the cells resuspended in 0.8 mls of the cold phage/Mg-PBS buffer suspension. The cell/phage suspension was added to a cold electroporation cuvette (BioRad 0.4 cm) and left on ice for 5 minutes. The cuvette was mixed by inverting 2–3 times. The electroporator was run at 240V, 500 uF and the suspension was left on ice for 20 minutes.

Each cell suspension was transferred into 15 mls of ES cell medium (EM-Dulbecco's Modified Eagles Medium and 10% fetal calf serum, BRL Gibco Gaithersberg Md.), mixed with a pipette and distributed into 5 prepared dishes containing 10 mls of media (supplemented with 1000 units of LIF (BRL Gibco, Gaithersberg Md.) per ml of media). Plate A (unselected control plate) received 50 μl of cells. Plate B (G418 only) received 500 μl of cells and plates C, D and E (double-crossover selection) received 5 mls of cells.

The following day the media was replaced with 20 mls of ES media supplemented with LIF. Two days after transfection the selection drug G418 at 300 μg/ml was added to plates B–E and the selection drug FIAU at 250 μg/ml was added to plates C–E. The ES clones appeared within 8 to 10 days.

$10^{11}$ phage particles (~5 μg DNA equivalents) gave approximately the same number of DNA transformants (~10,000) as 150 μg of naked DNA based on the same gene targeting vector and the same electroporation conditions. Screening of these clones resulted in a 52% targeting efficiency compared to a 7% frequency as naked DNA. This represents a 200 fold increase in gene targeting efficiency using intact bacteriophage based on DNA concentration as compared to electroporation of naked DNA (10% transformed).

Figure 5A:
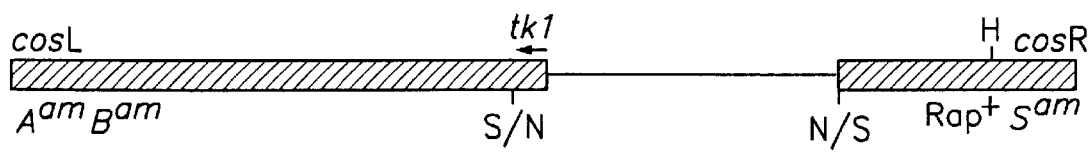
FIG. 5A illustrates the restriction map of λTK.

EXAMPLE 4
λTK-ES Cell Genomic Library for Single Step Targeting Vector Construction λTK is a recombinogenic targeting vector phage derived from λ2TK by removal of the HSV-2TK gene adjacent to the short arm. A diagram of the λTK library vector is shown in FIG. 5A. As with λ2TK, λTK is $A^{am}$, $B^{am}$ and $S^{am}$, requires the amber suppressor tRNA supF for lytic growth, is $Rap^+$ for efficient recombination with plasmid (15) and contains a $red^+$, $gam^+$ stuffer fragment for convenient cloning. λTK contains cosL/R cohesive sites on the left and right arms of the vector. λTK was constructed in order to generate a random isogenic ES cell genomic library in a gene targeting phage. The reduced size of λTK accommodates the cloning of moderately sized-random genomic fragments (12–15 kb) while still allowing the construction of neo and lacZneo targeting vectors by recombination screening methodologies.

An isogenic 129SV genomic library was developed in λTK using a partial fill-in method which adapted Sau3A genomic fragments into XhoI sites within λTK. Genomic DNA was isolated from a 129SV/J mouse and subjected to partial Sau3Z digestion. Digest DNA ws fractionated by sucrose gradient ultracentrifugation and dATP and Klenow enzyme and ligated to XhoI cut and G/T partially filled in λTK. The library was packaged using Gigapack Gold (Stratagene La Jolla Calif.) and $2.5 \times 10^6$ recombinant phage were amplified on P2392 over 60- 20 cm plates. The following day plate lysates were collected in SM buffer, cleared by centrifugation, pooled and frozen as 1 ml aliquots using 7% DMSO. After amplification of the library, the average insert size was found to be 13 kb. This library appears to be fairly representative of the ES cell genome. Genomic sequences have been successfully isolated for 9 out of 10 gene screened, with 2–3 isolates obtained for each gene.

EXAMPLE 5
Recombination Screening of an ES Library

Figure 5B:
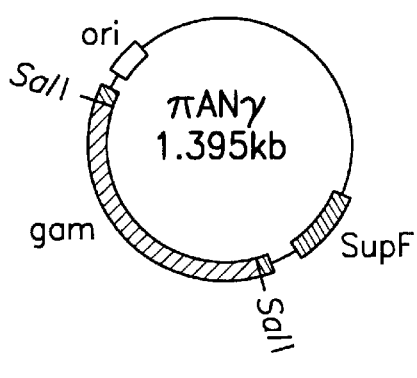
FIG. 5B illustrates the restriction map of πANγ.
Figure 5C:
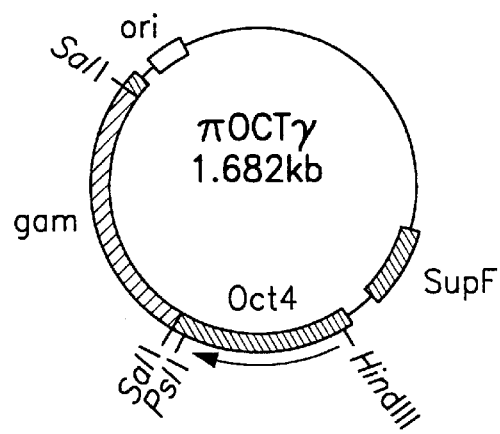
FIG. 5C illustrates the restriction map of πOCTγ.

The *E. coli* strain LG75 (25) is rec+; $supF^0$; $lacZ^{am}$, and therefore requires the presence of exogenous supF activity for lacZ expression. LG75 were provided by Dr. D. M. Kurnit (University of Michigan, Ann Arbor).

πANγ is a derivative of πAN13 (15) and contains the gam gene of bacteriophage λ subcloned into the SalI site of the pUC13 polycloning site (FIG. 5B). The introduction of the gamma gene allows negative selection for the plasmid sequence in P2392. The SupF gene allows growth of the recombinant phage as well as selection for co-integrates on host LG75. The probe plasmid πOCTγ (FIG. 5C) was created by ligation of a 268bp region from exon 1 of the mouse Oct4 gene (29) into the πANγ plasmid digested with HindIII and PstI. πOCT is essentially the same as πOCTγ, however the gam gene has been removed by SalI digestion.

πOCTγ was electroporated into MC1060[P3] host cells, and transformants were selected for on LB-AKT media (Ampicillin, Kanamycin, Tetracycline; 50 μg/mL working concentration each). Positve isolates were used to inoculate 2 mL of LB-AKT-maltose (0.2% maltose) liquid media, and this culture was subsequently used to inoculate a 20 mL LB-AKT-maltose liquid culture, which was grown to an $OD_{600}=0.6$ or 1.0. Cells from this culture were isolated by centrifugation, resuspended in 100 μL 10 mM $MgSO_4$, and infected with a 100 μL aliquot of the λTK-129 library described in Example 4 ($3 \times 10^8$ pfu/mL) at a phage:cell ratio of ~1:200. Whole culture lysis and phage-plasmid recombination (FIG. 6A) was allowed to continue in 40 mL NZY-Amp-maltose liquid media. The presence of only ampicillin in the culture media is sufficient to select for the maintenance of both the p3 episome and the probe plasmid, yet it also allows the bacteria to grow at a rate such that they may compete with the phage turnover. After 6–9 hours the remaining cells were lysed with 100 μL $CHCl_3$, and the phage were isolated in the supernatant, removing cellular debris by centrifugation. The titre was determined on LE392 (~$10^9$–$10^{10}$ pfu/mL), and the phage were passaged over LG75 on NZY media plus Xgal and IPTG (20 mg/mL each). Phage which had integrated the πOCTγ plasmid (and thus the SupF gene) via single cross-over homologous recombination through the Oct4 probe region (FIG. 6A) were selected for by their ability to form blue plaques on LG75. As shown in Table III, the recombination frequency for πOCTγ was approximately one order of magnitude higher than that seen for πOCT ($2.77 \times 10^{-6}$ vs. $2.53 \times 10^{-7}$)

TABLE III

| plasmid | phage titre[a] | # plaques (blue/white) | mean recombination frequency[c] |
|---|---|---|---|
| πOCTγ | $2.35 \times 10^{10}$ | 430/520 | $2.77 \times 10^{-6}$ |
|  |  | 214/163 |  |
|  | $4.1 \times 10^9$ | 150/970 |  |
|  |  | 191/469 |  |
| πOCT | $3.9 \times 10^{10}$ | 32/3000[b] | $2.53 \times 10^{-7}$ |
|  |  | 200/2800b |  |
|  | $5.0 \times 10^9$ | 10/560 |  |
|  |  | 15/298 |  |

[a]The phage titre is expressed as pfu/ml;
[b]1 μl of each phage lysate was used instead of 10 μL to derive these values
[c]recombination frequencies were determined for each individual data set using the following formula # blue plaques/(phage titre - # white plaques) and were then averaged for each plasmid.

Isolated positive plaques were placed in SM phage dilution buffer (Sambrook et al., 1989), and passaged over LE392 in 2 mL NZY-maltose liquid media. Integration of the plasmid into the homologous regions of the phage results in a duplication of homology which is then capable of undergoing a second recombination event which restores both the plasmid and phage to their native configurations. This event occurs at a relative frequency of approximately 1.0% under relaxed conditions (i.e. SupF host) (FIG. 6B). Phage were again isolated in the culture supernatant by centrifugation, and titred on LE392 and P2392 to determine the number of phage which had accurately condensed.

TABLE IV

| phage | titre on LE392[a] | titre on P2393[a] | % condensation[b] |
|---|---|---|---|
| 1 | $4.3 \times 10^{10}$ | $1.1 \times 10^9$ | 2.6 |
| 2 | $1.3 \times 10^{11}$ | $8.7 \times 10^8$ | 0.7 |
| 3 | $4.8 \times 10^{10}$ | $1.6 \times 10^9$ | 3.3 |
| 4 | $2.9 \times 10^{10}$ | $8.4 \times 10^8$ | 2.9 |
| 5 | $7.0 \times 10^{10}$ | $1.0 \times 10^9$ | 1.4 |
| 6 | $4.0 \times 10^{104.0}$ | $9.4 \times 10^8$ | 2.4 |
| 7 | $4.7 \times 10^{10}$ | $1.4 \times 10^9$ | 3.0 |
| 8 | $5.6 \times 10^{10}$ | $4.1 \times 10^8$ | 0.7 |
|  |  | mean % | 2.1 |

[a]expressed as pfu/ml
[b]percent condensation was determined by the following formula: titre on P2392/tire on LE392

Plaques formed on a P2392 bacterial lawn by these phage were isolated in SM phage dilution buffer. Small scale phage DNA preparations and restriction endonuclease digestions were carried out to determine phage clone identity. Southern transfer and analysis with radiolabeled probes was used to provide a more detailed confirmation. The mean frequency of condensation was found to be 2.1%.

It has also been found that the condensation event need not be carried out under relaxed conditions in the host LE392. If recombinant phage from the blue plaques on LG75 are immediately passaged over P2392, a small number of plaques form, which represent gam⁻ phage. Thus it appears that the relaxed conditions simply allow a larger number of phage to undergo condensation.

EXAMPLE 6
Transplacement Mutagenesis

The recombination plasmid πANI3 (15; supplied by ATCC) and its derivatives were harboured in the rec⁺ host MC106I[p3], and were selected for supF activity by virtue of amber mutations $Amp^{am}$, $Tet^{am}$ on the p3 episome.

Figures 8A, 8B:
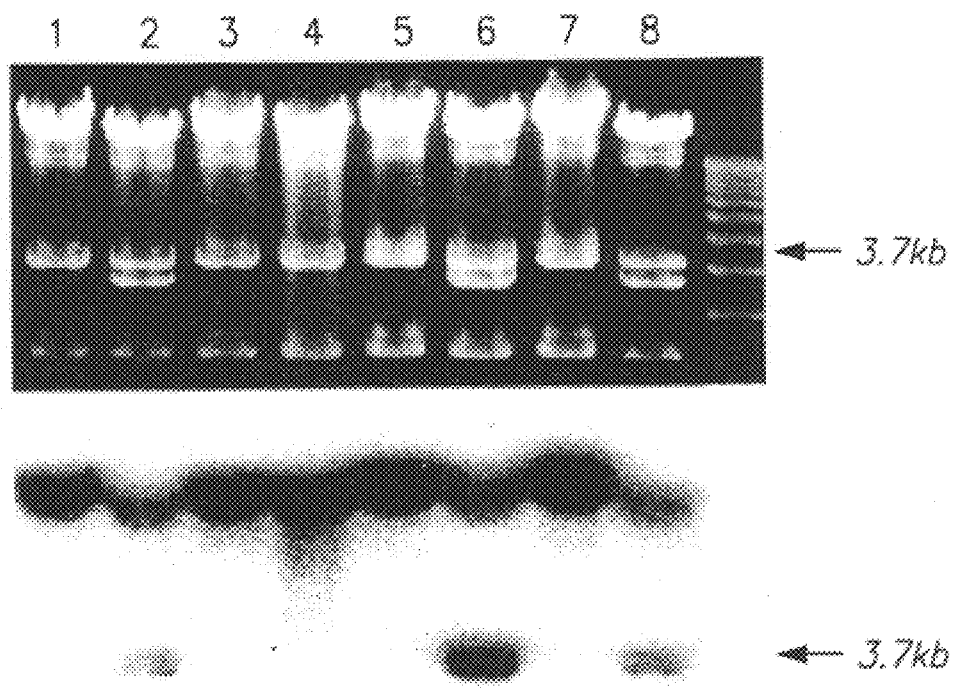
FIG. 8A is a photograph of a agarose gel stained with ethidium bromide of DNAs from phage/plasmid recombinants digested with NsiI. An extra band appears in three lanes (2, 6 and 8).
FIG. 8B is an autoradiograph of a Southern Blot of the same gel probed with a single-stranded SFD oligonucleotide probe.

The tester recombination plasmid πSFDγ (FIG. 7A) was generated by inserting a double-stranded oligonucleotide (bearing 50 bp of homology to the $5^{th}$ exon of TIMP3) into πANγ between Xba I and Bam HI sites. Centered within the 50 bp homology region was a 2 bp substitution which generated a diagnostic Nsi I site and mimicked the Serl8ICys mutation commonly found in Sorsby Fundus Dystrophy (30; FIG. 7B) [SEQ ID NOS: 1–5 ]. The tester bacteriophage vector λTK (FIG. 7C) has a 14 kb stuffer region flanked by XhoI sites. The λTKTIMP3 phage was isolated from a murine ES library and contains a 12 kb insert containing exons 2 to 5 of the mouse TIMP3 gene (FIG. 7D).

λTK:TIMP3 phage ($1 \times^4$ pfu) were passaged over MCIO6I[P3] bearing πSFDγ via overnight plate lysate at 37° C. Supernatant phage were collected the next day in phage dilution buffer and used to infect the indicator strains LE392, for titre determination and LG75 (with Xgal and IPTG) to select for single crossover recombinant phage (blue plaques), which were collected in phage dilution buffer. Recombinant phage where then passaged briefly in liquid culture (~six hours) under non-selective conditions using LE392, to allow condensation of the integrated plasmid. Condensatants were then selected for the absence of the gam gene (i.e. the recombination plasmid) by plating on P2392. To establish the authenticity of the apparent condensatants, individual spi- phage were isolated from plates and analysed by Nsi I restriction analysis to identify condensatants bearing the SFD point mutation. Transfer of the point mutation to these phages was also confirmed by Southern analysis using the SFD oligonucleotide as a probe. The fidelity of the region surrounding the transferred point mutation was also confirmed by cycle sequencing (ABI Prism). All of the eight phage had excised the plasmid via condensation and three of the eight phage had acquired the NsiI restriction site via transplacement recombination. In FIG. 8A, an extra band of about 3.7 kb appears in lanes 2, 6 and 8 of the gel. The extra band was clearly labelled in all three lines when a Southern Blot of the gel was probed with a single-stranded SFD oligonucleotide probe. (FIG. 8B) DNA sequencing of the transplaced phage clone demonstrated that only the designed SFD mutation was transferred to these phages, confirming the high fidelity of this in situ mutagenesis technique. The frequency of transplacement was less than 50%.

In transplacement of other perfectly centered point mutations to different genes, transplacement frequencies occurred at 35% and 50%. These results suggest that the frequency of transplacement may be optimized by choosing sequences around the mutation that are balanced in length and GC content.

EXAMPLE 7
Combination of Screening and Transplacement Mutagenesis

This experiment was used to demonstrate that TIMP3 specific phages could first be isolated from the λTK-129 library by recombination screening after which an Nsi I restriction site (and SFD mutation) could be deposited into specific phages following condensation.

$3 \times 10^8$ phages from the λTK-129 library were passaged over MC1061 [p3, πSFDγ] and recombinant phage were selected as blue plaques on LG75 as described herein. Isolated positive plaques were placed in SM phage dilution buffer and passaged over LE392 in 2 mL NZY-maltose liquid media to allow condensation under relaxed conditions. Phage lysates were then passaged over P2392 to isolate condensatants using spi selection. DNA from condensatants was used to confirm the presence of the Nsi I restriction site (and SFD mutation) in TIMP3 locus within the λTK targeting vector phage via restriction digestion and Southern blot analysis. The Nsi I point mutation was transferred to the phage at approximately 50% frequency.

EXAMPLE 8
Single Crossover Targeting Vectors via Recombination Screening

Targeting vectors were also generated in a single step using recombination screening. Recombination plasmids πneo and πGFPneo which are also derivatives of πan13 (15). A small amount of homology (50 bp) derived from oligonucleotides was cloned into the recombination plasmid. The library was passaged over the recombination plasmid and targeting vectors were isolated genetically in a single step.

πneo was generated by inserting a polymerase II-neo Hind III cassette (22) into the Hind III site of πAN13 (15). πGFPneo was generated by adapting the Enhanced Green Flurorescent Protein (EGFP) gene cassette from pEGFP1 (Clonetech), after which the EGFP cassette was introduced into πneo using the restriction enzymes EcoRI and XhoI. An Afl II compatible linker bearing an internal Xho I site was introduced into Afl II cut pEGFP-1, after which the EGFP cassette was excised with EcoR1 and Xho I and transferred into πneo. The resulting ligation retained several of the restriction sites originally upstream the EGFP cassette in pEGFP-1.

Single crossover was used to generate a knockout targeting vector for the gene p33ING1 (31). Two oligonucleotides [SEQ ID NOS:6 and 7] derived against the conserved region of p33ING1 gene 5' A A T T C G C G C T C C C T G C C G A C T T T C-
CCATCGACCCCAACGAGCCCACGTACT-
GTCTGA Bgl II EcoR1 CGCGAGGGACGGCT-
GAAAGGGTAGCTGGGGTTGCTCGGGTGCATGACAGACTCT
5' were annealed to form a double-stranded oligonucleotide and cloned between the EcoR1 and BamHI sites of πneo. The resulting plasmid was harbored in MC1061 (p3) as above. Initial experiments to investigate single crossover vectors were performed using a p33ING1 targeting vector clone isolated from λTK-129 library (above). $1 \times 10^3$ pfu of λTK-ING6 were passaged over MC1061 (p3) bearing the πneo-ING recombination plasmid by plate amplification on NZY ampicillin media overnight at 37 ° C. after which phage were harvested in SM phage dilution buffer by plate lysate.

Approximately $1 \times 10^3$ pfu of the resultant phage were plated on the restrictive host LG75 and single crossover recombinant phage were identified as blue plaques (as above). Southern analysis of the resulting recombinant phage DNAs was performed to confirm the site specific integration of the πneo-ING recombination plasmid into the λTK-ING6 phage. A resulting λTK-ING πneo6 targeting vector was prepared for electroporation into ES cells by restriction of the phage arms as set forth herein. Following positive-negative selection, 24 targeted ES cell lines were identified from a total of 108 ES cell clones by genomic Southern blot analysis using restriction sites and probes flanking the targeted locus (4).

πneo-ING recombination plasmid was also used to pull targeting vectors from the λTK-129 library by recombination screening. The λTK-129 library (3×10$^8$ pfu) was passaged over MC1061 [p3, πneo-ING] in liquid culture overnight. The following day, small aliquots (1–100 µl) of the cleared lysate were passaged over LG75 to identify blue plaques representing single-crossover recombinants. Due to the 500 bp of polB promoter sequence in πneo, a majority of the single crossover plaques (~90%) represented λTK-polB targeting vector clones. These were eliminated from the screen on the basis of plaque hybridization using polB-specific cDNA sequence following which p33ING1-specific targeting vectors were identified by Southern analysis.

While the above method is useful, there is a commercial concern that condensation of the single crossover insertion within the ES cell or animal after gene targeting could result in a reversion of the targeted mutation. Due to the small amount of homology (50 bp) that is used in this method, this is unlikely.

EXAMPLE 9

Double-Crossover Targeting Vectors via Recombination Screening

Targeting vectors were also pulled from the library via double-crossover recombination. The original double-crossover plasmid pGamCRABPneoF was used to pull multiple λTK:CRABPneo targeting vectors from the λTK-129 genomic library via double-crossover recombination screening.

The λTK-129 library (3×10$^8$ pfu) was passaged over MC 1061 [p3,pGamCRABPneoF] in liquid culture overnight. The following day, 100 µl aliquotes of the cleared lysate representing 1×10$^9$ pfu were passaged over LG75 to identify a handful of blue plaques representing double-crossover recombinants. Southern blot analysis of DNA isolated from the recombinant plaques confirmed that the neoF gene had site specifically integrated into the cRABPI locus by double-crossover recombination.

While the present invention has been described with reference to what are considered to be the preferred examples, it is to be understood that the invention is not limited to the disclosed examples. To the contrary, the invention is intended to cover various modifications and equivalent arrangements included within the spirit and scope of the appended claims.

REFERENCES

1. Capecchi, M. R. (1989) *Science*, 244:1288–1292.
2. Capecchi, M. R. (1989) *Trends Genet.*, 5:70–76.
3. Humphries et al. (1997). *Nature Genet.*, 15:216–219.
4. Thomas, K. R. and Capecchi, M. R. (1987) *Cell*, 51:503–512.
5. Mansour et al. (1990) *Proc. Natl. Acad. Sci.* 87:7688–7692.
6. Hanks et al. (1995) *Science*, 269:679–682.
7. Hasty et al. (1991) *Nature*, 350:243–246.
8. Mombaerts et al. (1991) *Proc. Natl. Acad. Sci.*, 88:3084–3087.
9. Ramirez-Solis et al. (1995) *Nature*, 378:720–724.
10. Tsien et al., (1996) *Cell*, 87:1317–1326.
11. Mansour, et al. (1988) *Nature*, 336:348–352.
12. Nagy, A. and Rossant, J. (1996) *J. Clin Invest.*, 98:S31–35.
13. Deng, C. and Capecchi, M. R. (1992) *Mol. Cell. Biol.*, 12:3365–3371.
14. Chisaka, O. and Capecchi, M. R. (1991) *Nature*, 350:473–479.
15. Lutz, et al. (1987) *Proc. Natl. Acad. Sci.*, 84:4379–4383.
16. Wei, et al. (1990) *DNA Cell. Biol.*, 9:471–478.
17. Seed, B. (1983) *Nucleic Acids Res.*, 11:2427–2445.
18. Maniatis, et al. (1982) Molecular Cloning: A Laboratory Manual. Cold Spring Harbor University Press, Cold Spring Harbor, N.Y.
19. Haggard-Ljungquist, et al. (1989) *Gene*, 85:25–33.
20. Zheng, H. and Wilson, J. H. (1990) *Nature*, 344:170–173.
21. Nehls, et al. (1994) *BioTechniques*, 17:770–775.
22. Rancourt, et al. (1995) *Genes Dev.*, 9, 108–122.
23. Umene, et al. (1979) *J. Bacteriol.*, 139:738–747.
24. Gorry, et al. (1994) *Proc. Natl. Acad. Sci.*, 91:9032–9036.
25. Shen, P. and Huang, H. V. (1986) *Genetics*, 112:441–457.
26. U. S. Pat. No. 5,487,992, Capecchi et al.
27. Zabarovsky et al. (1986) *Gene* 42:119.
28. Sternberg and Hoess, (1995) *PNAS USA* 92(2):1609–1613
29. Yeom et al., (1991) "Structure, expression and chromosomal location of the Oct-4 gene" *Mech. Dev.* 35:171–179
30. Weber et al.,(1994) *Natl. Genet* 8:352–356
31. Garkavtsev et al., (1996) "Suppression of the novel growth inhibitor p33$^{ING1}$ promotes neoplastic transformation" *Nature Genetics* 14:415–420

All publications, patents and patent applications are herein incorporated by reference in their entirety to the same extent as if each individual publication, patent or patent application was specifically and individually indicated to be incorporated by reference in its entirety.

What is claimed is:

1. A method for selection of a lambda bacteriophage having a desired target nucleic acid sequence from an assortment of bacteriophage wherein the bacteriophage comprise different nucleic acid inserts, said method comprising the following steps:
   (a) providing a plasmid, which plasmid comprises a portion of the desired target nucleic acid sequence, a prokaryotic positive selectable marker gene and a double-crossover selectable marker,
   (b) providing an assortment of bacteriophage comprising different nucleic acid inserts;
   (c) contacting the assortment of bacteriophage with the plasmid under conditions such that homologous recombination between the target nucleic acid sequence on the plasmid and the desired target nucleic acid sequence on the bacteriophage can occur;
   (d) growing the bacteriophage in bacterial cells under conditions wherein those bacteriophage which have recombined with the plasmid are able to replicate;
   (e) growing the bacteriophage from step (d) in bacterial cells under conditions wherein those bacteriophage lacking the double-crossover selectable marker are able to replicate; and
   (f) identifying those recombinant bacteriophage from step (e) as comprising the desired target nucleic acid.

2. The method of claim 1 wherein the double-crossover selectable marker gene is gam and the recombinant bacteriophage is grown in a P2 lysogenic bacterial cell in step (e).

3. The method of claim 1 wherein the prokaryotic positive selectable marker is selected from the group consisting of supF and supE genes and the bacteriophage further comprises amber mutations.

4. The method of claim 1 wherein the plasmid further comprises a eukaryotic positive selectable marker inserted into the target nucleic acid sequence.

5. The method of claim 4, wherein the eukaryotic positive selectable marker is selected from the group consisting of Neo, Hyg, hisD, Gpt, Ble and Hprt genes.

6. The method of claim 1 wherein the bacteriophage further comprises a eukaryotic negative selectable marker.

7. The method of claim 6 wherein the eukaryotic negative selectable marker is selected from the group consisting of the tk1 or tk2 genes.

8. The method of claim 1 wherein the prokaryotic positive selectable marker is selected from the group consisting of supF and supE genes.

9. A method for generating recombinant λ bacteriophage vectors, which method comprises:
   (a) providing a λ bacteriophage nucleic acid sequence comprising a first target nucleic acid sequence;
   (b) providing a plasmid comprising:
      (i) a nucleic acid sequence encoding a second modified target nucleic acid sequence wherein the second modified target nucleic acid sequence is substantially homologous over a portion of its length to the first target nucleic acid sequence,
      (ii) a prokaryotic positive selectable marker inserted into the target nucleic acid sequence, and
      (iii) a gam gene outside of the second modified target nucleic acid sequence;
   (c) contacting the bacteriophage and the plasmid under conditions such that homologous recombination between the first target nucleic acid sequence and the second target nucleic acid sequence occurs;
   (d) selecting for double-crossover recombinant bacteriophage by growing the bacteriophage from step (c) in a P2 lysogenic bacterial cell under conditions which select for bacteriophages harboring the prokaryotic positive selectable marker.

10. The method of claim 9 wherein the prokaryotic positive selectable marker is selected from the group consisting of supF and supE genes.

11. The method of claim 9 wherein the prokaryotic positive selectable marker is selected from the group consisting of supF and supE genes and the bacteriophage further comprises an amber mutation.

12. The method of claim 9 wherein the plasmid further comprises a eukaryotic positive selectable marker inserted into the target nucleic acid sequence.

13. The method of claim 12, wherein the eukaryotic positive selectable marker gene is selected from the group consisting of Neo, Hyg, hisD, Gpt, Ble and Hprt genes.

14. The method of claim 9 wherein the bacteriophage further comprises a eukaryotic negative selectable marker.

15. The method of claim 14 wherein the eukaryotic negative selectable marker is selected from the group consisting of the tk1 or tk2 genes.

* * * * *